United States Patent
Finlay et al.

(10) Patent No.: US 10,597,370 B2
(45) Date of Patent: Mar. 24, 2020

(54) 2-(BENZOTHIAZOL-2-YL)-2-CYANO-ACETAMIDE DERIVATIVES AND THEIR USE AS ENDOTHELIAL LIPASE INHIBITORS

(71) Applicant: BRISTOL-MYERS SQUIBB COMPANY, Princeton, NJ (US)

(72) Inventors: Heather Finlay, Skillman, NJ (US); Wei Meng, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/302,158

(22) PCT Filed: Jun. 5, 2017

(86) PCT No.: PCT/US2017/035880
§ 371 (c)(1),
(2) Date: Nov. 16, 2018

(87) PCT Pub. No.: WO2017/214005
PCT Pub. Date: Dec. 14, 2017

(65) Prior Publication Data
US 2019/0144403 A1    May 16, 2019

Related U.S. Application Data

(60) Provisional application No. 62/346,048, filed on Jun. 6, 2016.

(51) Int. Cl.
*A61K 31/428*    (2006.01)
*C07D 277/64*    (2006.01)
*C07D 417/10*    (2006.01)
*C07D 513/04*    (2006.01)
*C07D 417/04*    (2006.01)
*C07D 417/14*    (2006.01)

(52) U.S. Cl.
CPC ......... *C07D 277/64* (2013.01); *C07D 417/04* (2013.01); *C07D 417/10* (2013.01); *C07D 417/14* (2013.01); *C07D 513/04* (2013.01)

(58) Field of Classification Search
None
See application file for complete search history.

(56) References Cited

FOREIGN PATENT DOCUMENTS

EP    2351744 A1    8/2011

*Primary Examiner* — Samantha L Shterengarts
(74) *Attorney, Agent, or Firm* — Hong Liu

(57) ABSTRACT

The present invention provides compounds of Formula (I): as defined in the specification and compositions comprising any of such novel compounds. These compounds are endothelial lipase inhibitors which may be used as medicament.

(I)

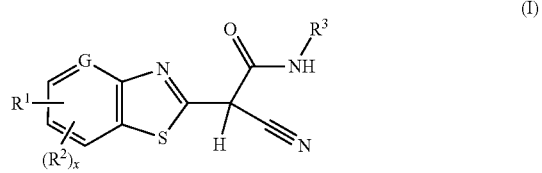

17 Claims, No Drawings

2-(BENZOTHIAZOL-2-YL)-2-CYANO-ACETAMIDE DERIVATIVES AND THEIR USE AS ENDOTHELIAL LIPASE INHIBITORS

CROSS-REFERENCE TO RELATED APPLICATIONS

This application is a 371 application of PCT/US2017/035880 filed Jun. 5, 2017 which claims the benefit of priority to U.S. Provisional Application Ser. No. 62/346,048, filed Jun. 6, 2016, the entire content of which is hereby incorporated by reference.

FIELD OF THE INVENTION

The present invention provides novel cyanomethyl linked benzothiazole compounds and analogues, which are endothelial lipase (EL) inhibitors, compositions containing them, and methods of using them, for example, for the treatment of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., *Nature*, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., *N. Engl. J. Med.*, 321(19):1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., *Trends Endocrinol. Metab.*, 13(4): 174-178 (2002); Wong, H. et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., *J. Biol. Chem.*, 274(20):14170-14175 (1999); Jaye, M. et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye, M. et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755 A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448 A1) and imidazopyridin-2-one derivatives (WO 2007/110215, US 2009/0076068 A1), and azolopyridin-3-one derivatives (WO 2007/110216, US 2009/0054478 A1) by Sanofi-Aventis; heterocyclic derivatives (WO 2009/123164), keto-amide derivatives (WO 2009/133834), acetic acid amide derivatives (WO 2010/044441, US 2011/0251386 A1) and oxadiazole derivatives (WO 2011/074560) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of modulating, e.g., inhibiting, the activity of lipases, particularly endothelial lipase, that would constitute effective treatments to the diseases or disorders associated with the activity of such lipases.

SUMMARY OF THE INVENTION

The present disclosure provides cyanomethyl linked benzothiazole compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment of dyslipidemias and the sequelae thereof.

The compounds of the invention may be used in therapy.

The compounds of the invention may be used for the manufacture of a medicament for the treatment of dyslipidemias and the sequelae thereof.

The compounds of the invention can be used alone, in combination with other compounds of the present invention, or in combination with one or more, e.g., one to two, other agent.

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

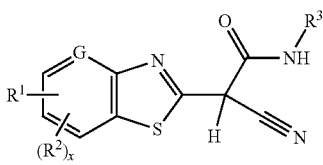

(I)

or a stereoisomer, a tautomer, or a pharmaceutically acceptable salt or a solvate thereof, wherein:

G is N or C;

$R^1$ is phenyl, a 5- or 6-membered heteroaryl, or a 5- or 6-membered non-aromatic heterocyclyl; wherein the heteroaryl or non-aromatic heterocyclyl each independently comprises one or more carbon atoms and 1 to 4 heteroatoms selected from N, $NR^a$, O, and $S(O)_Z$, and the phenyl, heteroaryl or non-aromatic heterocyclyl is each independently substituted with 0, 1, 2, or 3 $R^6$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NR^bR^c$, $NO_2$, $CO_2R^d$, and $CONR^bR^c$;

$R^3$ is $—(CH_2)_Y—CONR^eR^4$;

$R^e$ is hydrogen, $C_{1-4}$ alkyl, or $C_{3-6}$ carbocyclyl;

$R^4$ is $C_{1-6}$ alkyl substituted with 0, 1, or 2 $R^7$, $—(CH_2)_Q—(C_{3-6}$ carbocyclyl substituted with 0, 1, or 2 $R^7$), or $—(CH_2)_Q$-(4- to 6-membered heterocyclyl comprising one or more carbon atoms and 1 to 4 heteroatoms selected from N, $NR^a$, O, and $S(O)_Z$, wherein the heterocycle is substituted with 0, 1, or 2 $R^7$; or alternatively, $R^e$ and $R^4$, taken together with the atoms to which they are attached, form a 5- or 6-membered azacyclyl comprising one or more carbon atoms and 1 to 4 heteroatoms selected from N, $NR^a$, O, and $S(O)_Z$, wherein the azacyclyl is substituted with 0, 1, or 2 $R^5$;

$R^6$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NR^jR^9$, OPh, OBn, Ph, and $—CONR^hR^i$; or alternatively, two $R^6$, taken together with the atoms to which they are attached, form a 5- or 6-membered carbocyclyl, heteroaryl or non-aromatic heterocyclyl; wherein the heteroaryl or non-aromatic heterocyclyl each independently comprises one or more carbon atoms and 1 to 4 heteroatoms selected from N, $NR^a$, O, and $S(O)_Z$, and the carbocyclyl, heteroaryl or non-aromatic heterocyclyl is each independently substituted with 0, 1, 2, or 3 $R^8$;

$R^5$, $R^7$, $R^8$, and $R^9$ are, independently at each occurrence, selected from: OH, halogen, $C_{1-6}$ alkyl, $C_{1-4}$ alkoxy, $C_{1-4}$ haloalkyl, $C_{1-4}$ haloalkoxy, $NR^jR^k$, OPh, OBn, Ph, and a 5- or 6-membered heteroaryl comprising one or more carbon atoms and 1 to 4 heteroatoms selected from N, $NR^a$ and O;

$R^a$, $R^b$, $R^c$, $R^d$, $R^e$, $R^j$, and $R^k$ are, independently at each occurrence, hydrogen, $C_{1-4}$ alkyl, or $C_{3-6}$ carbocyclyl;

$R^f$ and $R^g$ are independently hydrogen, $C_{1-4}$ alkyl, $C_{3-6}$ carbocyclyl, $CO_2R^m$, or $CONR^nR^p$;

$R^h$ and $R^i$ are independently hydrogen, $C_{1-4}$ alkyl, $C_{3-6}$ carbocyclyl, $C_{1-4}$ alkoxy, $C_{1-4}$ haloalkyl, $C_{1-4}$ haloalkoxy; or alternatively, $R^h$ and $R^i$, taken together with the atoms to which they are attached, form a 5- or 6-membered azacyclyl comprising one or more carbon atoms and 1 to 4 heteroatoms selected from N, $NR^a$, O, and $S(O)_Z$, wherein the azacyclyl is substituted with 0, 1, or 2 $R^9$;

$R^m$, $R^n$, and $R^p$ are independently hydrogen, $C_{1-4}$ alkyl, $C_{3-6}$ carbocyclyl, $C_{1-4}$ alkoxy, $C_{1-4}$ haloalkyl, $C_{1-4}$ haloalkoxy, aryl, arylalkyl, or a 5- or 6-membered heteroaryl comprising one or more carbon atoms and 1 to 4 heteroatoms selected from N, $NR^a$ and O;

X is 0, 1, 2, or 3;

Y is 1, 2, or 3;

Z is, independently at each occurrence, 0, 1, or 2; and

Q is, independently at each occurrence, 0, 1, 2 or 3.

In a second aspect, the present invention includes a compound of Formula (IIa) or (IIb):

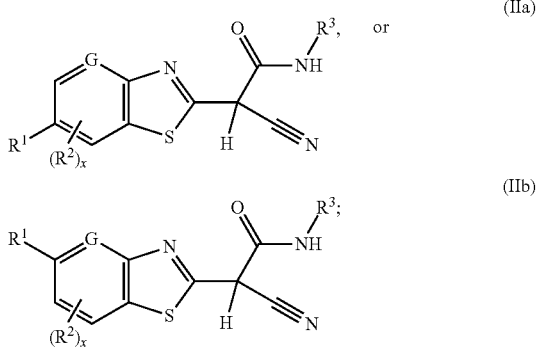

or a stereoisomer, a tautomer, a pharmaceutically acceptable salt, or a solvate thereof, within the scope of the first aspect, wherein G is N or C; m is 0, 1, or 2; and $R^2$ is, independently at each occurrence, selected from: halogen, $C_{1-4}$ alkyl, $C_{1-4}$ alkoxy, $C_{1-4}$ haloalkyl, and $C_{1-4}$ haloalkoxy.

In a third aspect, the present invention includes a compound of Formula (I), (IIa), or (IIb), or a stereoisomer, a tautomer, a pharmaceutically acceptable salt, or a solvate thereof, within the scope of the first or second aspect, wherein: $R^1$ is phenyl, pyridinyl, pyrrolidinonyl, or pyridinonyl, each of which is independently substituted with 0, 1, 2, or 3 $R^6$.

In a fourth aspect, the present invention includes a compound of Formula (I), (IIa), or (IIb), or a stereoisomer, a tautomer, a pharmaceutically acceptable salt, or a solvate thereof, within the scope of any of the above aspects, wherein:

$R^3$ is $—(CH_2)_Y—CONH(C_{3-6}$ carbocyclyl substituted with 0, 1, or 2 $R^7$), $—(CH_2)_Y—CONH(4$- to 6-membered heterocyclyl substituted with 0, 1, or 2 $R^7$), or $—(CH_2)_Y—CONR^eR^4$; Y is 1 or 2; and $R^e$ and $R^4$, taken together with the atoms to which they are attached, form a 5- or 6-membered azacyclyl, which is substituted with 0, 1, or 2 $R^5$.

In a fifth aspect, the present invention includes a compound of Formula (I), (IIa), or (IIb), or a stereoisomer, a tautomer, a pharmaceutically acceptable salt, or a solvate thereof, within the scope of any of the above aspects, wherein:

$R^3$ is $—(CH_2)_Y—CONH(C_{3-6}$ cycloalkyl substituted with 0, 1, or 2 $R^7$), $—(CH_2)_Y—CONH(4$- to 6-membered heterocycloalkyl substituted with 0, 1, or 2 $R^7$), or $—(CH_2)_Y—CONR^eR^4$; Y is 1; and $R^e$ and $R^4$, taken together with the atoms to which they are attached, form azetidinyl, pyrrolidinyl, piperidinyl, morpholinyl, or piperazinyl, each of which is substituted with 0, 1, or 2 $R^5$.

In a sixth aspect, the present invention includes a compound of Formula (I) or (II), or a stereoisomer, a tautomer, a pharmaceutically acceptable salt, or a solvate thereof, within the scope of any of the above aspects, wherein:

$R^6$ is not present or $R^6$ is OH, halogen, $C_{1-6}$ alkyl, $C_{1-4}$ alkoxy, $C_{1-4}$ haloalkyl, $NH_2$, $NHR^g$, and $—CONR^hR^i$;

$R^g$ is $C_{1-4}$ alkyl, $CO_2R^m$, $CONHR^p$, or $CONR^nR^p$;

$R^h$ and $R^i$ are independently hydrogen, $C_{1-4}$ alkyl, $C_{1-4}$ alkoxy, $C_{1-4}$ haloalkyl, $C_{1-4}$ haloalkoxy; or alternatively, $R^h$ and $R^i$, taken together with the atoms to which they are attached, form a 5- or 6-membered azacyclyl comprising one or more carbon atoms and 1 to 4 heteroatoms selected from N, $NR^a$, O, and S(O)Z, wherein the azacyclyl is substituted with 0, 1, or 2 $R^9$; and $R^m$, $R^n$, and $R^p$ are independently $C_{1-4}$ alkyl, $C_{1-4}$ alkoxy, $C_{1-4}$ haloalkyl, or $C_{1-4}$ haloalkoxy.

In a seventh aspect, the present invention includes a compound of Formula (I), (IIa), or (IIb), or a stereoisomer, a tautomer, a pharmaceutically acceptable salt, or a solvate thereof, within the scope of the fifth aspect, wherein:

$R^3$ is $-(CH_2)_Y-CONHR^4$; and $R^4$ is cyclopropyl, cyclobutyl, cyclopentyl, oxetanyl, tetrahydrofuranyl, tetrahydropyranyl, azetidinyl, pyrrolidinyl, piperidinyl, morpholinyl, or piperazinyl, each of which is substituted with 0, 1, or 2 $R^7$.

In an eighth aspect, the present invention includes a compound of Formula (I), (IIa), or (IIb), or a stereoisomer, a tautomer, a pharmaceutically acceptable salt, or a solvate thereof, within the scope of the sixth aspect, wherein $R^h$ and $R^i$ are, taken together with the atoms to which they are attached, form azetidinyl, pyrrolidinyl, piperidinyl, morpholinyl, or piperazinyl, each of which is independently substituted with 0, 1, or 2 $R^9$.

In a ninth aspect, the present invention includes a compound of Formula (IIIa) or (IIIb),

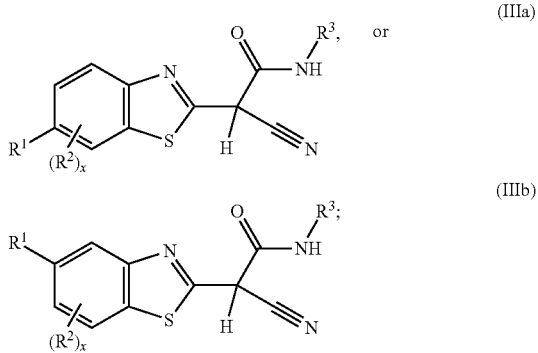

or a stereoisomer, a tautomer, a pharmaceutically acceptable salt, or a solvate thereof, within the scope of the first aspect, wherein $R^1$ is phenyl, pyridinyl, pyrrolidinonyl, or pyridinonyl; wherein the phenyl, pyridinyl, or pyridinonyl is each independently substituted with 0 or 1 $R^6$;

$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NH_2$, $NH(C_{1-4}$ alkyl), $NO_2$, $CO_2H$, $CO_2(C_{1-4}$ alkyl), $CONH_2$, and $CONH(C_{1-4}$ alkyl);

$R^3$ is $-(CH_2)-CONH(C_{3-6}$ carbocyclyl substituted with 0, 1, or 2 $R^7$), $-(CH_2)_Y-CONH$(4- to 6-membered heterocyclyl substituted with 0, 1, or 2 $R^7$), or $-(CH_2)_Y-CONR^eR^4$;

$R^e$ and $R^4$, taken together with the atoms to which they are attached, form a 5- or 6-membered azacyclyl comprising one or more carbon atoms and 1 to 4 heteroatoms selected from N, $NR^a$, O, and S(O)Z, wherein the azacyclyl is substituted with 0, 1, or 2 $R^5$;

$R^6$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, $NHR^g$, OPh, OBn, Ph, $-CONH_2$; $-CONHR^i$; and $-CONR^hR^i$; or alternatively, two $R^6$, taken together with the atoms to which they are attached, form a 5- or 6-membered heterocyclyl; wherein the heterocyclyl comprises one or more carbon atoms and 1 to 4 heteroatoms selected from N, $NR^a$, O, and S(O)Z, and is substituted with 0, 1, 2, or 3 $R^8$;

$R^7$, $R^8$, and $R^9$ are, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, $NH(C_{1-4}$ alkyl), OPh, OBn, Ph, and a 5- or 6-membered heteroaryl comprising one or more carbon atoms and 1 to 4 heteroatoms selected from N, $NR^a$ and O;

$R^a$ is, independently at each occurrence, hydrogen, $C_{1-4}$ alkyl, or $C_{3-6}$ carbocyclyl;

$R^g$ is $C_{1-4}$ alkyl, $CO_2H$, $CO_2R^m$, $CONH_2$; $CONHR^p$;

$R^i$ is $C_{1-4}$ alkyl, $C_{1-4}$ alkoxy, $C_{1-4}$ haloalkyl, $C_{1-4}$ haloalkoxy; or alternatively, $R^h$ and $R^i$, taken together with the atoms to which they are attached, form a 5- or 6-membered azacyclyl comprising one or more carbon atoms and 1 to 4 heteroatoms selected from N, $NR^a$, O, and $S(O)_Z$), wherein the azacyclyl is substituted with 0, 1, or 2 $R^9$;

$R^m$ and $R^p$ are independently $C_{1-4}$ alkyl, $C_{3-6}$ carbocyclyl, $C_{1-4}$ alkoxy, $C_{1-4}$ haloalkyl, $C_{1-4}$ haloalkoxy, OPh, OBn, Ph, and a 5- or 6-membered heteroaryl comprising one or more carbon atoms and 1 to 4 heteroatoms selected from N, $NR^a$ and O;

X is 0, 1, or 2;

Y is 1 or 2;

Z is, independently at each occurrence, 0, 1, or 2; and

Q is, independently at each occurrence, 0 or 1.

In a tenth aspect, the present invention includes a compound of Formula (IIIa), or (IIIb), or a stereoisomer, a tautomer, a pharmaceutically acceptable salt, or a solvate thereof, within the scope of the ninth aspect, wherein $R^3$ is $-(CH_2)-CONH(C_{3-6}$ cycloalkyl substituted with 0, 1, or 2 $R^7$), $-(CH_2)-CONH$(4- to 6-membered heterocycloalkyl substituted with 0, 1, or 2 $R^7$), or $-(CH_2)-CONR^eR^4$; and $R^e$ and $R^4$, taken together with the atoms to which they are attached, form a 5- or 6-membered azacyclyl comprising one or more carbon atoms and 1 to 4 heteroatoms selected from N, $NR^a$, O, and S(O)Z, wherein the azacyclyl is substituted with 0, 1, or 2 $R^5$.

In an eleventh aspect, the present invention includes a compound of Formula (IIIa) or (IIIb), or a stereoisomer, a tautomer, a pharmaceutically acceptable salt, or a solvate thereof, within the scope of the tenth aspect, wherein $R^3$ is $-(CH_2)-CONHR^4$; and $R^4$ is cyclopropyl, cyclobutyl, cyclopentyl, oxetanyl, tetrahydrofuranyl, tetrahydropyranyl, azetidinyl, pyrrolidinyl, piperidinyl, morpholinyl, or piperazinyl, each of which is substituted with 0 or 1 $R^7$; or alternatively, $R^3$ is $-(CH_2)-CONR^eR^4$; and $R^e$ and $R^4$, taken together with the atoms to which they are attached, form azetidinyl, pyrrolidinyl, piperidinyl, morpholinyl, or piperazinyl, each of which is substituted with 0, 1, or 2 $R^5$.

In a twelfth aspect, the present invention includes a compound of Formula (IIIa) or (IIIb), or a stereoisomer, a tautomer, a pharmaceutically acceptable salt, or a solvate thereof, within the scope of the ninth and tenth aspects, wherein $R^h$ and $R^i$, taken together with the atoms to which they are attached, form azetidinyl, pyrrolidinyl, piperidinyl, morpholinyl, or piperazinyl, each of which is substituted with 0, 1, or 2 $R^9$.

In a thirteenth aspect, the present invention includes a compound of Formula (IIIa) or (IIIb), or a stereoisomer, a tautomer, a pharmaceutically acceptable salt, or a solvate thereof, within the scope of any of the ninth, tenth, eleventh, and twelfth aspects, wherein:

$R^6$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, $NHR^g$, OPh, OBn, Ph, —$CONH_2$, —$CONHR^i$; and —$CONR^hR^i$; or alternatively, two $R^6$, taken together with the atoms to which they are attached, form pyrrolidinonyl or pyridinonyl; each of which is substituted with 0, 1, or 2 $R^8$;

$R^g$ is $C_{1-4}$ alkyl, $CO_2R^m$, or $CONHR^p$;

$R^i$ is $C_{1-4}$ alkyl, $C_{1-4}$ alkoxy, $C_{1-4}$ haloalkyl, $C_{1-4}$ haloalkoxy; or alternatively, $R^h$ and $R^i$, taken together with the atoms to which they are attached, form azetidinyl, pyrrolidinyl, piperidinyl, morpholinyl, or piperazinyl, each of which is substituted with 0, 1, or 2 $R^9$;

$R^m$ and $R^p$ are independently $C_{1-4}$ alkyl, $C_{1-4}$ alkoxy, $C_{1-4}$ haloalkyl, or $C_{1-4}$ haloalkoxy; and Q is 0.

In a fourteenth aspect, the present invention includes a compound of Formula (IIIa) or (IIIb), or a stereoisomer, a tautomer, a pharmaceutically acceptable salt, or a solvate thereof, within the scope of the first or ninth aspect, wherein $R^1$ is selected from the group consisting of

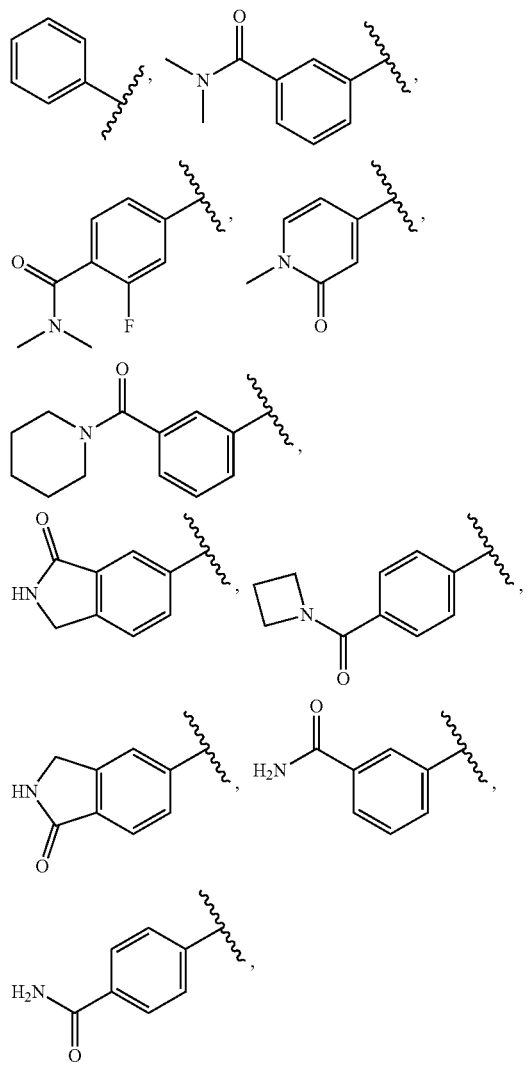

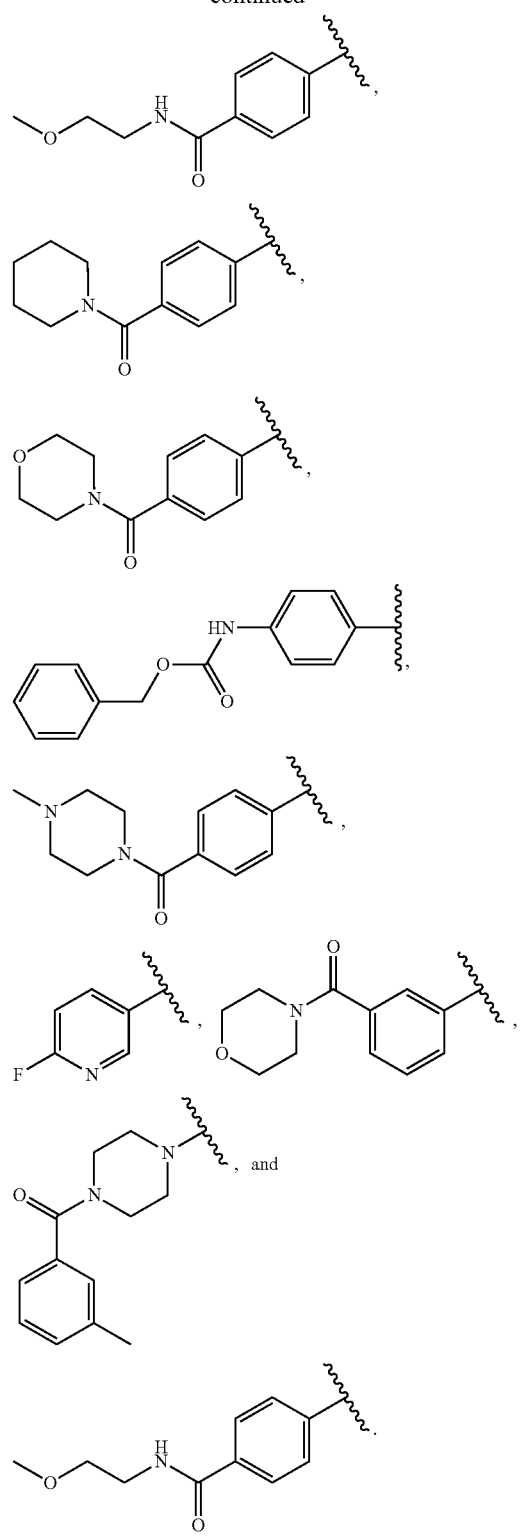

In a fifteenth aspect, the present invention includes a compound of Formula (IIIa) or (IIIb), or a stereoisomer, a tautomer, a pharmaceutically acceptable salt, or a solvate thereof, within the scope of the first or ninth aspect, wherein $R^3$ is selected from the group consisting of

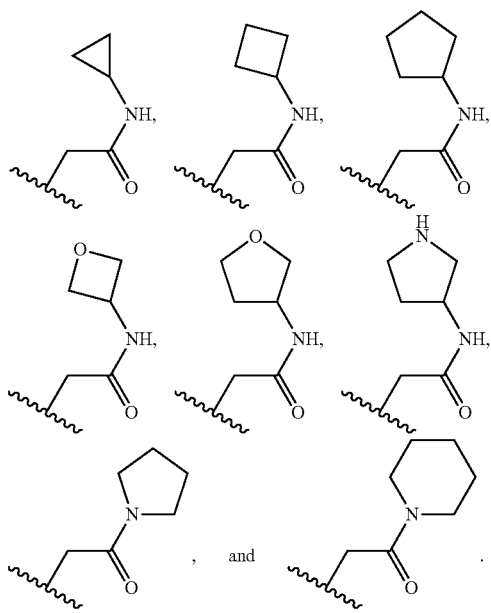

, and

In another aspect, the present invention provides a compound selected from any subset list of compounds or a single compound from the exemplified examples, or a stereoisomer, a tautomer, a pharmaceutically acceptable salt, or a solvate thereof, within the scope of the first or ninth aspect.

In another embodiment, the compounds of the present invention have EL $IC_{50}$ values ≤500 nM.

In another embodiment, the compounds of the present invention have EL $IC_{50}$ values ≤200 nM.

In another embodiment, the compounds of the present invention have EL $IC_{50}$ values ≤100 nM.

In another embodiment, the compounds of the present invention have EL $IC_{50}$ values ≤50 nM.

In another embodiment, the compounds of the present invention have EL $IC_{50}$ values ≤25 nM.

In another embodiment, the compounds of the present invention have EL $IC_{50}$ values ≤10 nM.

II. Other Embodiments of the Invention

In another embodiment, the present invention provides a composition comprising at least one of the compounds of the present invention or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of endothelial lipase in a patient in need such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of dyslipidemias and the sequelae thereof comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment of atherosclerosis, coronary heart disease, cerebrovascular disorders and dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of dyslipidemias and the sequelae thereof.

In another embodiment, the present invention also provides the use of a compound of the present invention for the manufacture of a medicament for the treatment of dyslipidemias and the sequelae thereof.

In another embodiment, the present invention provides a method for the treatment of dyslipidemias and the sequelae thereof, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds of Formula (I), (IIa), (IIb), (IIIa), or (IIIb), a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and iso-propoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. That is, the term "carbocycle", "carbocyclyl", or "carbocyclic residue" includes both aromatic carbocyclyl, such as aryl, and non-aromatic carbocyclyl, such as cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aromatic carbocyclyl" or "aryl" refers to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemi-* cal Dictionary, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$. "Benzyl" can also be represented by formula "Bn".

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. That is, the term "heterocycle", "heterocyclyl", or "heterocyclic group" includes both aromatic heterocyclyl, such as heteroaryl, and non-aromatic heterocyclyl, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclyl" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

In accordance with a convention used in the art,

is used in structural formulas herein to depict the bond that is the point of attachment of the moiety or substituent to the core or backbone structure.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, the ketone (—C—C=O) group in a molecule may exist in different tautomeric forms and or different hydrate forms, wherein $R^1$, $R^2$ and $R^4$ are as defined above:

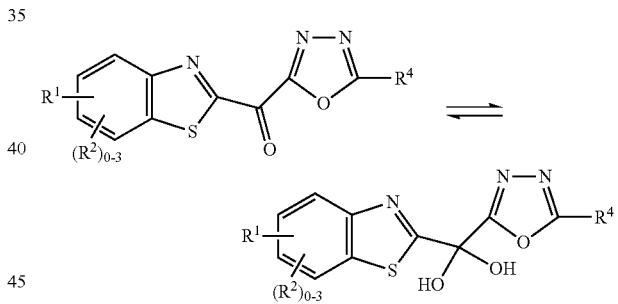

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of Formula (I), Formula (IIa), Formula (IIb), Formula (IIIa), or Formula (IIIb) may have prodrug forms. Any compound that will be converted in vivo to provide the bioactive agent (i.e., a compound of Formula (I), Formula (IIa), Formula (IIb), Formula (IIIa), or Formula (IIIb)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "13", "R", "S", "E", and "Z" are stereochemical designations familiar to one skilled in the art.

AcOH or HOAc acetic acid

ACN acetonitrile

Alk alkyl
BBr$_3$ boron tribromide
Bn benzyl
Boc tert-butyloxycarbonyl
BOP reagent benzotriazol-1-yloxytris(dimethylamino)phosphonium hexafluorophosphate
Bu butyl
i-Bu isobutyl
t-Bu tert-butyl
t-BuOH tert-butanol
Cbz carbobenzyloxy
CDCl$_3$ deutero-chloroform
CD$_3$OD deutero-methanol
CH$_2$Cl$_2$ dichloromethane
CH$_3$CN acetonitrile
CHCl$_3$ chloroform
DCM dichloromethane
DIEA, DIPEA or diisopropylethylamine
Hunig's base
DMF dimethyl formamide
DMSO dimethyl sulfoxide
Et ethyl
Et$_3$N or TEA triethylamine
Et$_2$O diethyl ether
EtOAc ethyl acetate
EtOH Ethanol
HATU 1-[Bis(dimethylamino)methylene]-1H-1,2,3-triazolo[4,5-b]pyridinium 3-oxide hexafluorophosphate
HCl hydrochloric acid
HPLC high-performance liquid chromatography
K$_2$CO$_3$ potassium carbonate
K$_2$HPO$_4$ potassium hydrogenphosphate
LCMS liquid chromatography mass spectrometry
LiHMDS lithium bis(trimethylsilyl)amide
LG leaving group
Me methyl
MeOH methanol
MgSO$_4$ magnesium sulfate
MsOH or MSA methylsulfonic acid
NaCl sodium chloride
Na$_2$CO$_3$ sodium carbonate
NaHCO$_3$ sodium bicarbonate
NaHMDS sodium hexamethyldisilazide
NaOH sodium hydroxide
Na$_2$SO$_4$ sodium sulfate
NH$_3$ ammonia
NH$_4$Cl ammonium chloride
NH$_4$OAc ammonium acetate
Pd(OAc)$_2$ palladium(II) acetate
Pd(PPh$_3$)$_4$ tetrakis(triphenylphosphine)palladium(0)
PG protecting group
Ph phenyl
Pr propyl
i-Pr isopropyl
i-PrOH or IPA Isopropanol
PyBOP benzotriazol-1-yl-oxytripyrrolidinophosphonium hexafluorophosphate
Rt retention time
SiO$_2$ silica oxide
SFC supercritical fluid chromatography
TEA triethylamine
TFA trifluoroacetic acid
THF tetrahydrofuran
TiCl$_4$ titanium tetrachloride
T3P 1-propanephosphonic acid cyclic anhydride
2nd generation XPHOS Chloro(2-dicyclohexylphosphino-2',4',6'-triisopropyl-1,1'-biphenyl) [2-(2'-amino-1,1'-biphenyl)]palladium(II) precatalyst Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated by references in their entirety for all purposes.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Wiley and Sons (1991)).

Generic Schemes

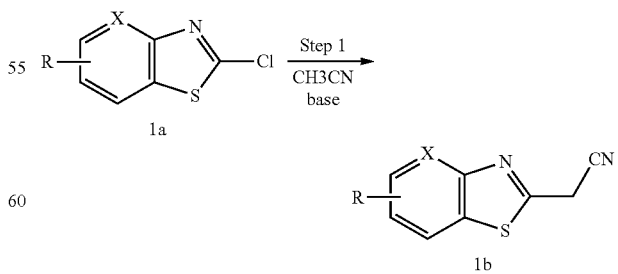

Step 1 describes the preparation of cyanomethyl compounds of formula 1b by reacting a chloride of formula 1a with acetonitrile under basic conditions. Chloride of formula 1a is either commercially available or can be readily prepared by those skilled in the art. An example to prepare substituted 2-chlorobenzo[d]thiazole can be found in Roehn, Ulrike et al., PCT Int. Appl., 2012007510. An example to prepare substituted 2-chlorothiazolo[4,5-b]pyridine can be found in Ye, Xiang-Yang et al., PCT Int. Appl., 2011140160. Preferred solvents for Step 1 are hydrocarbon and ethereal solvents such as hexanes, toluene, ether, toluene, dioxane and the like. Preferred bases include hydrides (such as sodium hydride and the like), metal amides (such as sodium or potassium hexamethyldisilazide, lithium diisopropylamide and the like) and organolithiums (such as butyllithium and the like). Temperature for the transformation can range from −78° C. to 50° C.

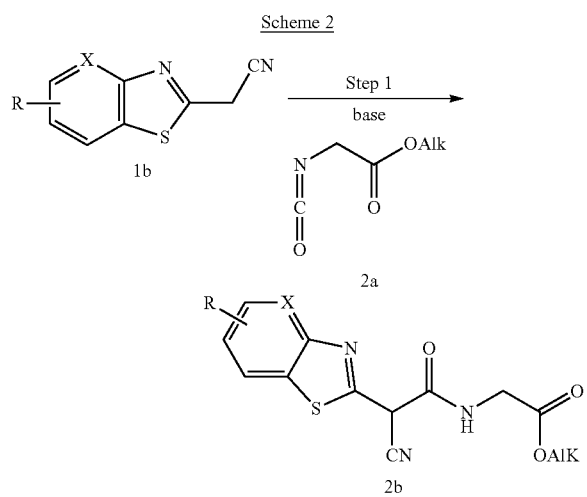

Step 1 describes the preparation of cyano and ester containing compounds of formula 2b by reacting of compounds of formula 1b with an isocyanate of formula 2a under basic conditions. Preferred solvents for Step 1 are hydrocarbon and ethereal solvents such as hexanes, toluene, ether, toluene, dioxane and the like. Preferred bases include hydrides (such as sodium hydride and the like) and metal amides (such as sodium or potassium hexamethyldisilazide, lithium diisopropylamide and the like). Temperature for the transformation can range from −78° C. to 80° C.

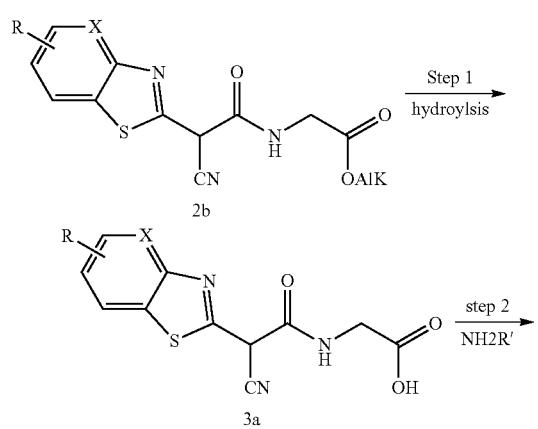

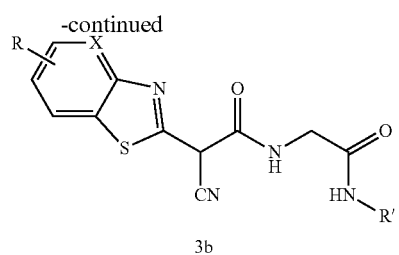

Step 1 describes hydrolysis of the esters of formula 2b to carboxylic acids of formula 3a. Preferred solvents are halogenated solvents (such as dichloromethane and the like) and water. Preferred reagents are acids (such as TFA, HCl and the like) or metal hydroxides (such as sodium hydroxide and the like). Temperature for the transformation can range from 0° C. to 100° C. Step 2 describes the conversion of an acid of formula 3a to an amide of formula 3b. A large number of amines of formula NH₂R' are commercially available. Preferred solvents for Step 1 are polar aprotic solvents (such as N,N-dimethylformamide), chlorinated solvents (such as dichloromethane and the like) and ethers (such as tetrahydrofuran, dioxane and the like). Preferred reagents are amide bond coupling reagents (such as EDC, HATU, PyBOP, T3P and the like). Temperature for the transformation can range from 0° C. to 50° C. Alternatively, the carboxylic acid of 3a can be activated initially to an acid chloride, mixed anhydride and the like, followed by reacting with amine NH₂R' to provide amides of formula 3b.

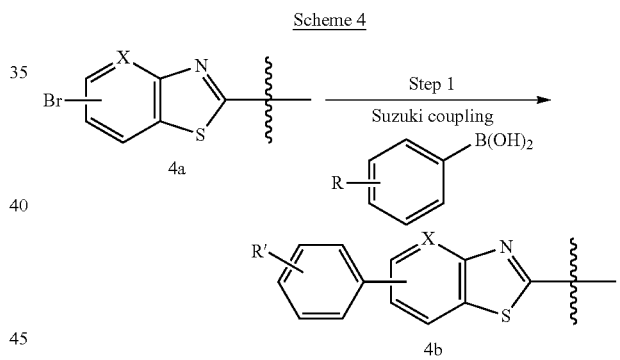

Step 1 describes the conversion of a bromide of formula 4a to a biphenyl like structure as represented by formula 4b through a Suzuki-type of reaction. This transformation has been recorded extensively in the literature and can be performed readily by those skilled in the art. A useful reference for this transformation can be found in Dennis G. Hall et al., *The Contemporary Suzuki-Miyaura Reaction*, Wiley, 2011. Boron based reagents as represented by, but not limited to, boronic acids, esters and the like, are mostly commercially available but can also be prepared readily by those skilled in the art. Preferred catalysts are palladium-based reagents (such as tetrakis(triphenylphosphine)palladium(0), 2nd generation XPHOS Precatalyst and the like). Preferred bases include carbonates (such as cesium carbonate and the like), phosphates (potassium phosphate, tribasic and the like) and amines (such as triethylamine and the like). Preferred solvents are polar aprotic solvents (such as N,N-dimethylformamide), and ethers (such as tetrahydrofuran, dioxane and the like). Temperature for the transformation can range from ambient to 150° C.

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm).

Purification of intermediates and final products was carried out via either normal or reverse phase chromatography. Normal phase chromatography was carried out using pre-packed $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 m C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Luna Axia 5 m C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 m C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 m C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Alternatively, reverse phase preparative HPLC was carried out using a VARIAN® ProStar Preparative HPLC System running Star 6.2 Chromatography Workstation software using Method E: Dynamax 10 m C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: Column: Waters Acquity UPLC BEH C18, 2.1×50 mm, 1.7 μm particles; Mobile Phase A: 5:95 ACN: water with 10 mM $NH_4OAc$; Mobile Phase B: 95:5 ACN: water with 10 mM $NH_4OAc$; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN: water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 m C18 (2.0×30 mm); Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B; Flow: 1 mL/min; Detection: UV at 220 nm.

Method D: Waters Acquity UPLC BEH C18, 2.1×50 mm, 1.7 μm particles; Mobile Phase A: water with 0.1% TFA; Mobile Phase B: ACN with 0.1% TFA; Gradient: 2-98% B over 1 minute, then a 0.5 minute hold at 98% B; Flow: 0.8 mL/min; Detection: UV at 220 nm.

Method E: A linear gradient using solvent A (10% MeOH, 90% water, 0.1% TFA) and solvent B (90% MeOH, 10% water, 0.1% TFA); 0-100% of solvent B over 4 min and then 100% of solvent B over 1 min. Column: PHENOMENEX® Luna 3 m C18 (2.0×50 mm). Flow rate was 0.8 mL/min.

Method F: A linear gradient using solvent A (5% ACN, 95% water, 0.05% TFA) and solvent B (95% ACN, 5% water, 0.05% TFA); 0-100% of solvent B over 12 min and then 100% of solvent B over 3 min. Column: SUNFIRE C18, 3 μm (3.0×150 mm). Flow rate was 1 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters Masslynx 4.0 SP4 MS software UV visualization at 220 nm Column: Waters XBridge 19×150 mm 5 m C18

Flow rate: 20 mL/min

Peak collection triggered by mass spectrometry

Solvent A: 0.1% TFA, 10% ACN, 90% water

Solvent B: 0.1% TFA, 90% ACN, 10% water

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 μm (4.6×150 mm). Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 m (4.6×150 mm). Flow rate was 2 ml/min. and UV detection was set to 220 nm. The LC column was maintained at room temperature.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}C$ NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., Science, 235:442-447 (1987); Yanagisawa, M. et al., Nature, 332(6163):411-415 (1988); Folkman, J. et al., J. Biol. Chem., 267(16):10931-10934 (1992); Janssens, S. P. et al., J. Biol. Chem., 267(21):14519-14522 (1992); Lamas, S. et al., Proc. Natl. Acad. Sci. U.S.A., 89(14):6348-6352 (1992); Luscher, T. F. et al., Hypertension, 19(2):117-130 (1992); Williams et al., Am. Rev. Respir. Dis., 146:S45-S50 (1992); and Bevilacqua, M. P. et al., J. Clin. Invest., 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., Circulation, 79(1):8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., Circulation, 106(11): 1321-1326 (2002)). Notably, the endothelial lipase-mediated binding and uptake of HDL particles and the selective uptake of HDL-derived cholesterol esters have been reported to be independent of its enzymatic lipolytic activity (Strauss, J. G. et al., Biochem. J., 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include preventative (e.g., prophylactic) and palliative treatment, such as (a) inhibiting the disease-state, i.e., arresting it development; (b) relieving the disease-state, i.e., causing regression of the disease state; and/or (c) alleviating one or more symptoms of the disease.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 μL of 1 mM DMPG in a 1:1 mixture of MeOH and $CHCl_3$ with 15 μL of 1 mM A10070 in a 1:1 mixture of MeOH and $CHCl_3$. The mixture was dried under nitrogen and resuspended in 150 μL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 μL of assay buffer (50 mM HEPES pH 8.0, 50 mM NaCl and 1 mM $CaCl_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 μL of a 1:4 dilution of vesicles. The final total reaction volume was 100 μL. The reaction rates were measured on a Gemini plate reader with an excitation wavelength of 488 nm and an emission of 530 nm. Readings were taken every 20 seconds for 10 min with agitation between each reading. The slope of the linear portion of the readout was used to calculate the rate of the reaction.

Comparator Compounds

The following comparator compound and the preparation is disclosed in WO 2011/074560. The EL $IC_{50}$ value is reported in WO 2011/074560.

Suggested Comparators:

| Example No. in WO 2011/074560 | Structure | EL $IC_{50}$ (nM) |
|---|---|---|
| I-3-21 | 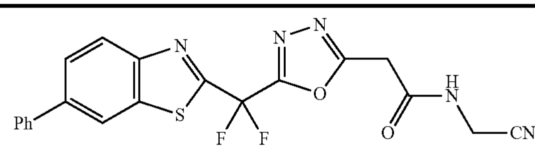 | 250 as reported in WO 2011/074560 |

The following reference compounds and their preparations are described below. The EL $IC_{50}$ values were measured using the EL assay described above.

Suggested Comparators:

| Reference | Structure | EL $IC_{50}$ (nM) |
|---|---|---|
| Reference 1 | 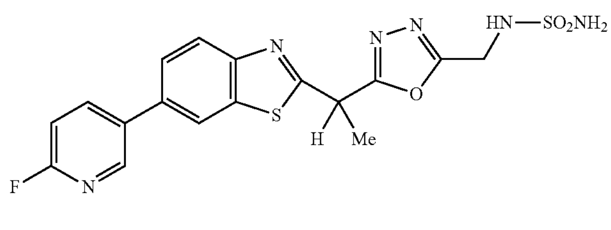 [SMILES: CC(c1nnc(CNS(N)(=O)=O)o1)c1nc2ccc(-c3ccc(F)nc3)cc2s1] | 6518 |
| Reference 2 | 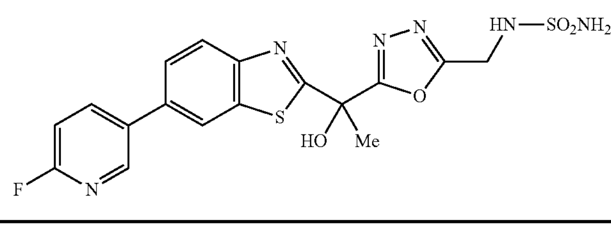 | 14880 |

The exemplified compounds, Examples 1 to 29, disclosed in the present invention were tested in the EL assay described above. Surprisingly, Examples 1 to 29 were found having a range of EL $IC_{50}$ values of ≤1 μM (1000 nM), as shown below.

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

IV. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent (s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent (s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Example 1. 2-cyano-N-(2-(cyclopropylamino)-2-oxoethyl)-2-(6-phenylbenzo[d]thiazol-2-yl)acetamide

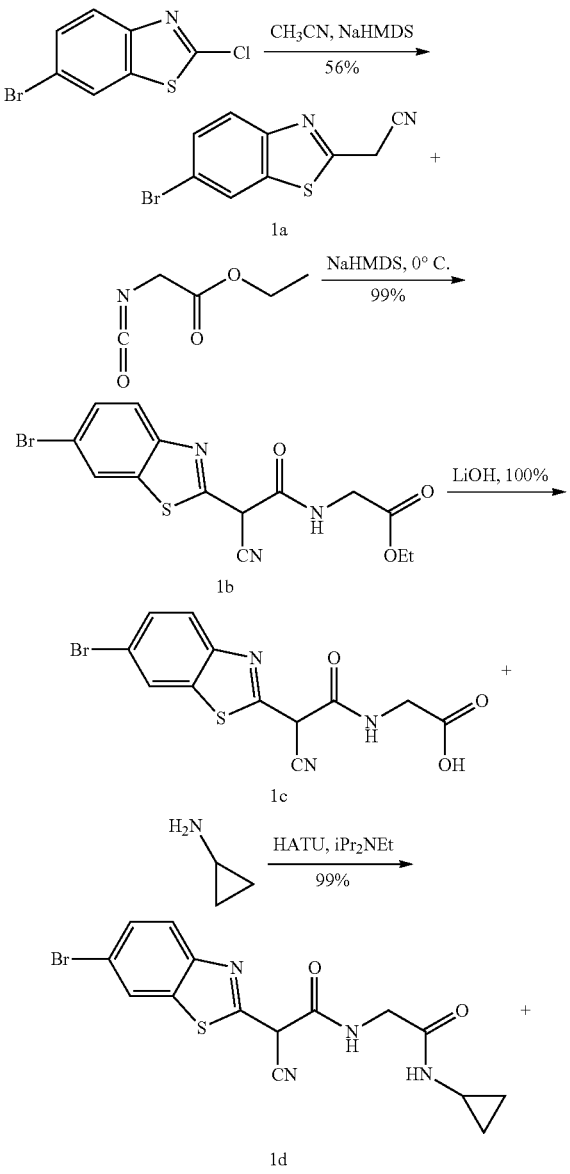

-continued

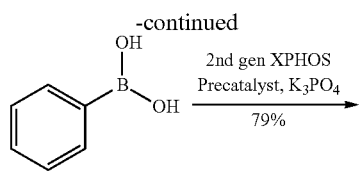

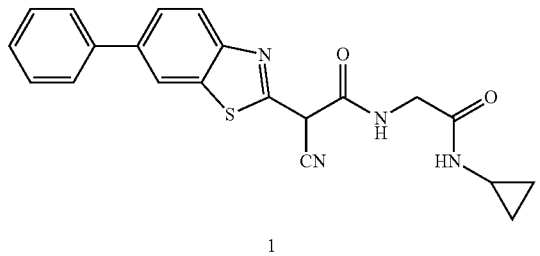

1

Compound 1a. 2-(6-bromobenzo[d]thiazol-2-yl)acetonitrile

To a stirred solution of 6-bromo-2-chlorobenzo[d]thiazole (3.0 g, 12 mmol) and acetonitrile (1.9 mL, 36 mmol) in toluene (16 mL) at 0° C. was added 1 M NaHMDS in THF (36 mL, 36 mmol). The reaction mixture was allowed to warm up to RT and stirred for 1 hr. The reaction mixture was concentrated in vacuo and the residue diluted with EtOAc. The organic layer was washed with $H_2O$. The organic layer was separated, dried over $MgSO_4$, filtered and concentrated in vacuo. The residue was recrystallized in EtOAc to give Compound 1a (1.7 g, 6.7 mmol, 56% yield) as a brown solid. MS m/z=254.9 (M+H). $^1$H NMR (500 MHz, $CDCl_3$) δ 8.05 (d, J=1.2 Hz, 1H), 7.90 (d, J=8.6 Hz, 1H), 7.64 (dd, J=2.0, 8.6 Hz, 1H), 4.22 (s, 2H).

Compound 1b. ethyl 2-(2-(6-bromobenzo[d]thiazol-2-yl)-2-cyanoacetamido)acetate

To a stirred solution of Compound 1a (510 mg, 2.0 mmol) in THF (5 mL) at 0° C. was added 1 M NaHMDS (2.4 mL, 2.4 mmol). After 20 min, ethyl 2-isocyanatoacetate (0.30 mL, 2.6 mmol) was added and the reaction mixture was allowed to warm to RT and stirred for 1 hr. The reaction mixture was concentrated in vacuo and diluted with EtOAc/THF. A precipitate formed and was filtered to collect 300 mg of Compound 1b. The filtrate organic layer was washed with saturated $NH_4Cl$ solution. The organic layer was separated, dried over $MgSO_4$, filtered and concentrated in vacuo. The residue was added to a silica gel (80 g) column and was eluted with 0-20% MeOH in DCM. Collected fractions to give additional Compound 1b (total 750 mg, 1.2 mmol, 99% yield) as a yellow solid. MS m/z=383.9 (M+H). $^1$H NMR (500 MHz, DMSO-d6) δ 8.07 (s, 1H), 7.75 (br s, 1H), 7.54 (d, J=8.8 Hz, 1H), 7.40 (d, J=8.5 Hz, 1H), 4.11 (q, J=7.2 Hz, 2H), 3.88 (d, J=5.8 Hz, 2H), 1.21 (t, J=7.2 Hz, 3H).

Compound 1c. 2-(2-(6-bromobenzo[d]thiazol-2-yl)-2-cyanoacetamido)acetic Acid

To a solution of Compound 1b (450 mg, 1.2 mmol) in THF (3 mL) was added lithium hydroxide monohydrate (0.10 mL, 3.5 mmol) in 1 mL water. The reaction mixture was stirred at ambient temperature for 2 hrs. The reaction mixture was concentrated in vacuo and diluted with EtOAc/THF. The organic layer was washed with 0.1 M HCl. The organic layer was separated, dried over $MgSO_4$, filtered and concentrated in vacuo to give Compound 1c (430 mg, 1.2 mmol, 100% yield) as a light brown solid. MS m/z=355.8 (M+H). $^1$H NMR (500 MHz, $CD_3OD$) δ 7.87 (s, 1H), 7.51 (d, J=8.5 Hz, 1H), 7.36 (br s, 1H), 6.92 (s, 1H), 3.99 (s, 2H).

Compound 1d. 2-(6-bromobenzo[d]thiazol-2-yl)-2-cyano-N-(2-(cyclopropylamino)-2-oxoethyl)acetamide Compound 1c (430 mg, 1.2 mmol) and cyclopropylamine (140 mg, 2.4 mmol) were dissolved in DMF (5 mL) and THF (15 mL). HATU (920 mg, 2.4 mmol) and Hunig's Base (0.60 mL, 3.6 mmol) were added, and the reaction mixture was stirred at ambient temperature for 2 hrs. The reaction mixture was concentrated in vacuo and diluted with EtOAc/THF. The organic layer was washed with 0.1 M HCl. The organic layer was separated, dried over $MgSO_4$, filtered and concentrated in vacuo. The residue was suspended in DCM and the resulting solid collected by filtration to generate Compound 1d as a tan solid (300 mg). Additional Compound 1d was isolated from the filtrate which was added to a silica gel (40 g) column and was eluted with 0-20% MeOH in DCM. Collected fractions to give additional Compound 1d (170 mg, 0.50 mmol, 99% yield) as a tan solid. MS m/z=394.9 (M+H). $^1$H NMR (500 MHz, DMSO-d6) δ 12.80 (s, 1H), 8.05 (s, 1H), 7.94 (s, 1H), 7.47-7.56 (m, 1H), 7.38 (br s, 1H), 3.71 (d, J=5.5 Hz, 2H), 2.61-2.65 (m, 1H), 0.59-0.63 (m, 2H), 0.40-0.43 (m, 2H).

Example 1. 2-cyano-N-(2-(cyclopropylamino)-2-oxoethyl)-2-(6-phenylbenzo[d]thiazol-2-yl)acetamide To a mixture of Compound 1d (85 mg, 0.20 mmol), phenylboronic acid (32 mg, 0.30 mmol), tripotassiumphosphate (140 mg, 0.60 mmol) and 2nd generation XPHOS precatalyst (17 mg, 0.020 mmol) was added dioxane (5 mL) and water (2 mL). The mixture was degassed with argon and heated at 90° C. for 1 hr. The reaction mixture was concentrated in vacuo. The residue was purified by prep HPLC (Phenomenex Luna AXIA 5 μm C18 30×100 mm column; detection at 220 nm; flow rate=40 mL/min; continuous gradient from 0% B to 100% B over 12 min+3 min hold time at 100% B, where A=90:10:0.1 $H_2O$:MeOH:TFA and B=90:10:0.1 MeOH:$H_2O$:TFA) to give Example 1 (67 mg, 0.20 mmol, 79% yield) as a white solid. The estimated purity by LCMS analysis was 99%, HPLC method F, RT=8.77 min, MS m/z=391.0 (M+H). $^1$H NMR (500 MHz, DMSO-d6) δ 12.83 (s, 1H), 8.18 (s, 1H), 8.02 (br s, 1H), 7.71-7.77 (m, 3H), 7.60 (d, J=8.3 Hz, 1H), 7.54 (d, J=7.7H, 1H), 7.53 (d, J=7.7 Hz, 1H), 7.42 (t, J=7.2 Hz, 1H), 7.38 (br s, 1H), 3.78 (d, J=5.5 Hz, 2H), 2.67-2.71 (m, 1H), 0.66-0.70 (m, 2H), 0.46-0.50 (m, 2H). EL $IC_{50}$=13 nM.

The following Examples 2 to 13, were prepared by the general procedures described for Example 1.

| Ex # | Structure | Name | NMR | LC/MS RT (min) method M + H | EL IC$_{50}$ (nM) |
|---|---|---|---|---|---|
| 2 | 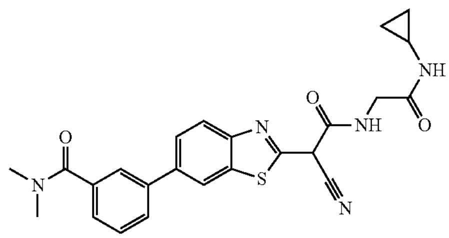 [SMILES: CN(C)C(=O)c1cccc(-c2ccc3nc(C(C#N)C(=O)NCC(=O)NC4CC4)sc3c2)c1] | 3-{2-[cyano({[(cyclopropyl-carbamoyl)methyl]carbamoyl})methyl]-1,3-benzothiazol-6-yl}-N,N-dimethyl-benzamide | 1H NMR (500 MHz, DMSO-d6) d 7.92 (s, 1H), 7.74 (s, 1H), 7.52 (d, J = 7.7 Hz, 1H), 7.40-7.50 (m, 2H), 7.27-7.30 (m, 2H), 7.13 (d, J = 7.1 Hz, 1H), 3.48 (d, J = 5.1 Hz, 2H), 2.77 (s, 3H), 2.71 (s, 3H), 2.39 (br s, 1H), 0.36-0.39 (m, 2H), 0.18 (br s, 2H) | 1.27 A 462.4 | 398 |
| 3 | 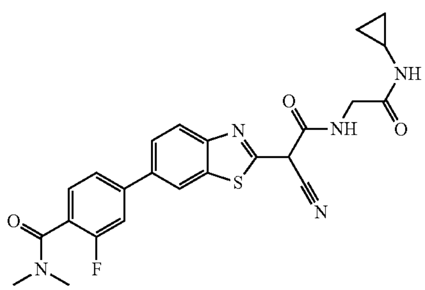 [SMILES: CN(C)C(=O)c1ccc(-c2ccc3nc(C(C#N)C(=O)NCC(=O)NC4CC4)sc3c2)cc1F] | 4-{2-[cyano({[(cyclopropyl-carbamoyl)methyl]carbamoyl})methyl]-1,3-benzothiazol-6-yl}-2-fluoro-N,N-dimethyl-benzamide | 1H NMR (500 MHz, DMSO-d6) d 8.22 (s, 1H), 8.00 (d, J = 3.7 Hz, 1H), 7.78 (d, J = 8.4 Hz, 1H), 7.62-7.66 (m, 2H), 7.56 (d, J = 8.4 Hz, 1H), 7.47 (t, J = 7.7 Hz, 1H), 7.39 (t, J = 5.4 Hz, 1H), 3.73 (d, J = 5.1 Hz, 2H), 3.03 (s, 3H), 2.90 (s, 3H), 2.63 (br s, 1H), 0.60-0.64 (m, 2H), 0.42 (br s, 2H) | 1.22 A 480.2 | 238 |
| 4 | 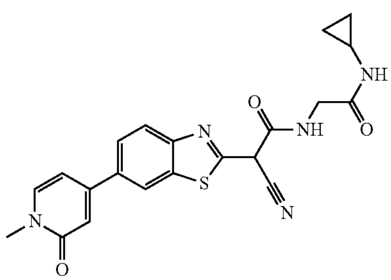 [SMILES: Cn1ccc(-c2ccc3nc(C(C#N)C(=O)NCC(=O)NC4CC4)sc3c2)cc1=O] | 2-cyano-N-[(cyclopropyl-carbamoyl)methyl]-2-[6-(1-methyl-2-oxo-1,2-dihydropyridin-4-yl)-1,3-benzothiazol-2-yl]acetamide | 1H NMR (500 MHz, DMSO-d6) d 12.84 (s, 1H), 8.22 (s, 1H), 7.96 (d, J = 3.9 Hz, 1H), 7.78 (d, J = 7.2 Hz, 1H), 7.76 (d, J = 9.6 Hz, 1H), 7.53 (d, J = 8.5 Hz, 1H), 7.37 (br s, 1H), 6.71 (d, J = 1.9 Hz, 1H), 6.61 (dd, J = 2.2, 7.2 Hz, 1H), 3.72 (d, J = 5.5 Hz, 2H), 3.45 (s, 3H), 2.60-2.67 (m, 1H), 0.60-0.64 (m, 2H), 0.41-0.44 (m, 2H) | 2.56 R 422.0 | >10,000 |
| 5 | 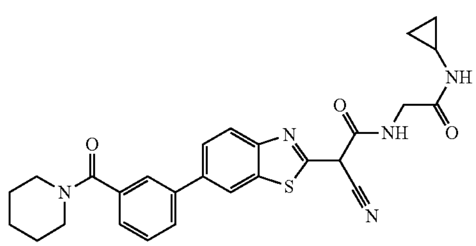 [SMILES: N#CC(C(=O)NCC(=O)NC1CC1)c1nc2ccc(-c3cccc(C(=O)N4CCCCC4)c3)cc2s1] | 2-cyano-N-[(cyclopropyl-carbamoyl)methyl]-2-{6-[3-(piperidine-1-carbonyl)phenyl]-1,3-benzothiazol-2-yl}acetamide | 1H NMR (500 MHz, CD3OD) d 8.03 (d, J = 7.9 Hz, 1H), 7.94 (d, J = 1.5 Hz, 1H), 7.74 (d, J = 8.4 Hz, 1H), 7.63-7.67 (m, 1H), 7.50-7.58 (m, 2H), 7.42 (d, J = 8.8 Hz, 1H), 7.33-7.39 (m, 2H), 7.13 (t, J = 7.0 Hz, 1H), 3.89 (s, 2H), 3.73 (br s, 2H), 3.42 (br s, 3H), 2.65-2.70 (m, 1H), 1.74 (br s, 4H), 1.56 (br s, 2H), 0.69-0.74 (m, 2H), 0.52-0.56 (m, 2H) | 3.43 R 502.0 | 16 |
| 6 | 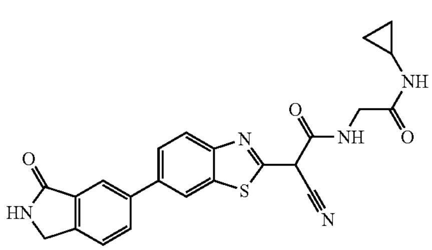 [SMILES: N#CC(C(=O)NCC(=O)NC1CC1)c1nc2ccc(-c3ccc4c(c3)C(=O)NC4)cc2s1] | 2-cyano-N-[(cyclopropyl-carbamoyl)methyl]-2-[6-(3-oxo-2,3-dihydro-1H-isoindol-5-yl)-1,3-benzothiazol-2-yl]acetamide | 1H NMR (500 MHz, DMSO-d6) d 12.79 (s, 1H). 8.60 (s, 1H), 8.20 (s, 1H), 7.90-7.99 (m, 3H), 7.73 (br s, 1H), 7.67 (d, J = 8.5 Hz, 1H), 7.56 (br s, 1H), 4.42 (s, 2H), 3.73 (d, J = 5.2 Hz, 2H), 2.61-2.67 (m, 1H), 0.60-0.64 (m, 2H), 0.41-0.44 (m, 2H) | 1.09 A 446.2 | 259 |

-continued

| Ex # | Structure | Name | NMR | LC/MS RT (min) method M + H | EL IC$_{50}$ (nM) |
|---|---|---|---|---|---|
| 7 | 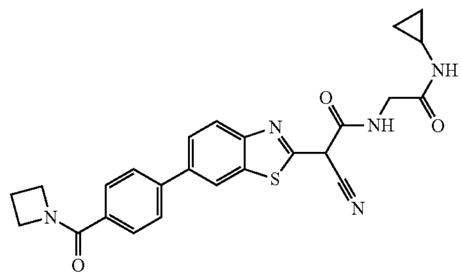 [SMILES: N#CC(C(=O)NCC(=O)NC1CC1)c1nc2ccc(-c3ccc(C(=O)N4CCC4)cc3)cc2s1] | 2-{6-[4-(azetidine-1-carbonyl)phenyl]-1,3-benzothiazol-2-yl}-2-cyano-N-[(cyclopropyl-carbamoyl)methyl]acetamide | 1H NMR (500 MHz, CD3OD) d 8.19 (s, 1H), 7.99 (s, 1H), 7.68-7.80 (m, 5H), 7.56 (d, J = 8.4 Hz, 1H), 7.37 (br s, 1H), 4.36 (t, J = 7.4 Hz, 2H), 4.07 (t, J = 7.1 Hz, 2H), 3.73 (d, J = 5.1 Hz, 2H), 2.59-2.67 (m, 1H), 2.25-2.31 (m, 2H), 0.59-0.65 (m, 2H), 0.42 (br s, 2H) | 1.27 A 474.1 | 15 |
| 8 | 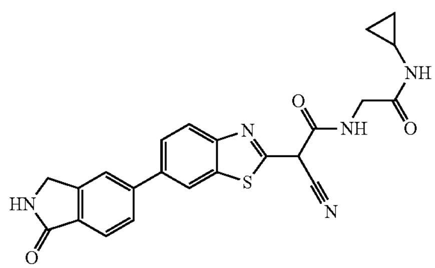 [SMILES: N#CC(C(=O)NCC(=O)NC1CC1)c1nc2ccc(-c3ccc4c(c3)CNC4=O)cc2s1] | 2-cyano-N-[(cyclopropyl-carbamoyl)methyl]-2-[6-(1-oxo-2,3-dihydro-1H-isoindol-5-yl)-1,3-benzothiazol-2-yl]acetamide | 1H NMR (500 MHz, DMSO-d6) d 8.56 (s, 1H), 8.17 (s, 1H), 7.97 (d, J = 3.7 Hz, 1H), 7.87 (s, 1H), 7.71-7.81 (m, 3H), 7.56 (d, J = 8.2 Hz, 1H), 7.35 (t, J = 5.2 Hz, 1H), 4.43 (s, 2H), 3.72 (d, J = 5.5 Hz, 2H), 2.62 (br s, 1H), 0.59-0.63 (m, 2H), 0.41 (br s, 2H) | 1.05 A 446.3 | 5 |
| 9 | 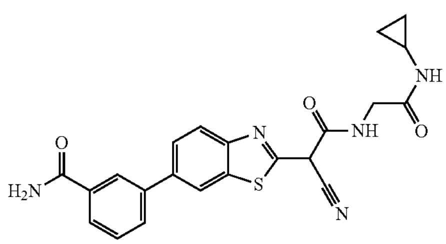 [SMILES: N#CC(C(=O)NCC(=O)NC1CC1)c1nc2ccc(-c3cccc(C(N)=O)c3)cc2s1] | 3-{2-[cyano({[(cyclopropyl-carbamoyl)methyl]carbamoyl})methyl]-1,3-benzothiazol-6-yl}benzamide | 1H NMR (500 MHz, DMSO-d6) d 8.18 (s, 2H), 8.12 (s, 1H), 7.98 (d, J = 2.1 Hz, 1H), 7.82-7.88 (m, 2H), 7.76 (d, J = 7.3 Hz, 1H), 7.55-7.58 (m, 2H), 7.43 (s, 1H), 7.34 (br s, 1H), 3.74 (d, J = 5.5 Hz, 2H), 2.60-2.67 (m, 1H), 0.61-0.65 (m, 2H), 0.41-0.44 (m, 2H) | 1.08 A 434.4 | 399 |
| 10 | 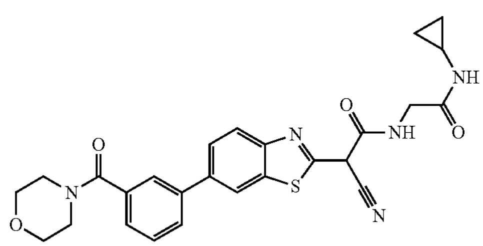 [SMILES: N#CC(C(=O)NCC(=O)NC1CC1)c1nc2ccc(-c3cccc(C(=O)N4CCOCC4)c3)cc2s1] | 2-cyano-N-[(cyclopropyl-carbamoyl)methyl]-2-{6-[3-(morpholine-4-carbonyl)phenyl]-1,3-benzothiazol-2-yl}acetamide | 1H NMR (500 MHz, DMSO-d6) d 8.18 (s, 1H), 7.98 (d, J = 3.7 Hz, 1H), 7.79 (d, J = 7.6 Hz, 1H), 7.74 (d, J = 8.2 Hz, 1H), 7.70 (s, 1H), 7.54-7.57 (m, 2H), 7.40 (d, J = 7.3 Hz, 1H), 7.34 (t, J = 5.2 Hz, 1H), 3.74 (d, J = 5.5 Hz, 2H), 3.53-3.70 (m, 8H), 2.61-2.67 (m, 1H), 0.61-0.65 (m, 2H), 0.41-0.45 (m, 2H) | 1.20 A 504.2 | 18 |
| 11 | 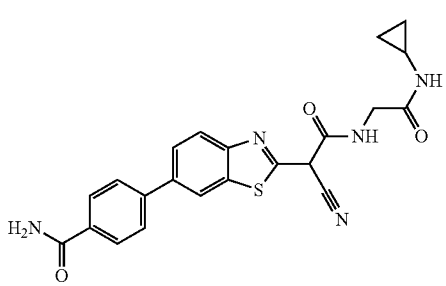 [SMILES: N#CC(C(=O)NCC(=O)NC1CC1)c1nc2ccc(-c3ccc(C(N)=O)cc3)cc2s1] | 4-{2-[cyano({[(cyclopropyl-carbamoyl)methyl]carbamoyl})methyl]-1,3-benzothiazol-6-yl}benzamide | 1H NMR (500 MHz, DMSO-d6) d 8.19 (s, 1H), 8.05 (s, 1H), 7.94-8.00 (m, 3H), 7.74-7.81 (m, 3H), 7.57 (d, J = 8.2 Hz, 1H), 7.37 (br s, 2H), 3.74 (d, J = 5.2 Hz, 2H), 2.62-2.65 (m, 1H), 0.61-0.65 (m, 2H), 0.41-0.44 (m, 2H) | 1.00 A 434.2 | 26 |

| Ex # | Structure | Name | NMR | LC/MS RT (min) method M + H | EL IC$_{50}$ (nM) |
|---|---|---|---|---|---|
| 12 | 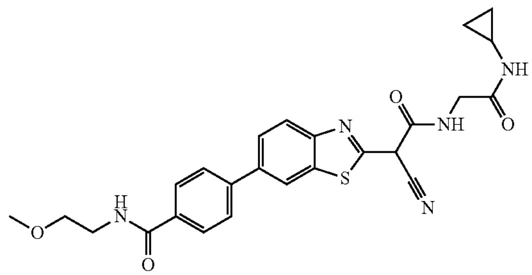 [SMILES: COCCNC(=O)c1ccc(-c2ccc3nc(C(C#N)C(=O)NCC(=O)NC4CC4)sc3c2)cc1] | 4-{2-[cyano ({[(cyclopropyl-carbamoyl) methyl] carbamoyl}) methyl]-1,3-benzothiazol-6-yl}-N-(2-methoxyethyl) benzamide | 1H NMR (500 MHz, DMSO-d6) d 8.58 (t, J = 5.2 Hz, 1H), 8.20 (s, 1H), 7.98 (br s, 1H), 7.95 (d, J = 8.2 Hz, 2H), 7.80 (d, J = 8.2 Hz, 2H), 7.77 (d, J = 8.5 Hz, 1H), 7.57 (d, J = 8.2 Hz, 1H), 7.34 (br s, 1H), 3.74 (d, J = 5.5 Hz, 2H), 3.46 (s, 4H), 2.61-2.66 (m, 1H), 0.61-0.65 (m, 2H), 0.41-0.44 (m, 2H) | 1.14 A 492.2 | 16 |
| 13 | 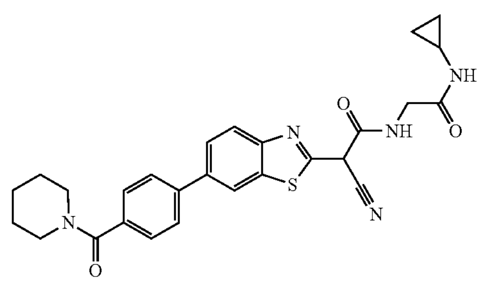 [SMILES: N#CC(C(=O)NCC(=O)NC1CC1)c1nc2ccc(-c3ccc(C(=O)N4CCCCC4)cc3)cc2s1] | 2-cyano-N-[(cyclopropyl-carbamoyl) methyl]-2-{6-[4-(piperidine-1-carbonyl) phenyl]-1,3-benzothiazol-2-yl} acetamide | 1H NMR (500 MHz, DMSO-d6) d 8.16 (s, 1H), 8.00 (d, J = 3.7 Hz, 1H), 7.73-7.76 (m, 3H), 7.57 (d, J = 8.5 Hz, 1H), 7.46 (d, J = 8.2 Hz, 2H), 7.36 (t, J = 5.5 Hz, 1H), 3.74 (d, J = 5.5 Hz, 2H), 3.46-3.52 (m, 4H), 2.61-2.66 (m, 1H), 1.60-1.68 (m, 2H), 1.43-1.60 (m, 4H), 0.61-0.65 (m, 2H), 0.43 (br s, 2H) | 1.43 A 502.4 | 11 |

Example 14. 2-cyano-N-(2-(cyclopropylamino)-2-oxoethyl)-2-(6-(4-(morpholine-4-carbonyl)phenyl) benzo[d]thiazol-2-yl)acetamide

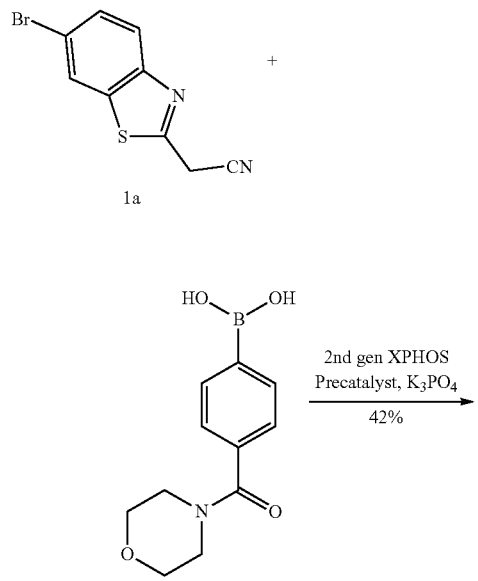

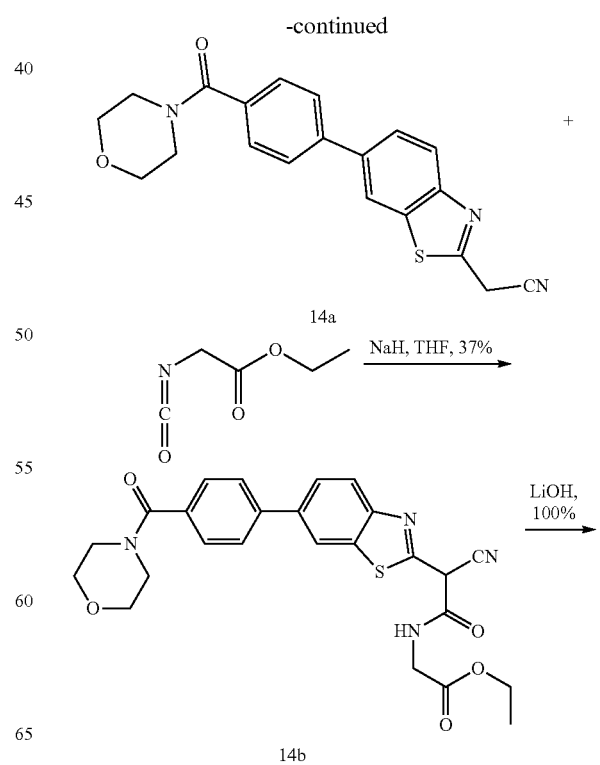

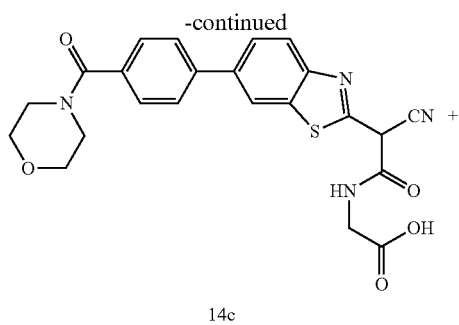

14c

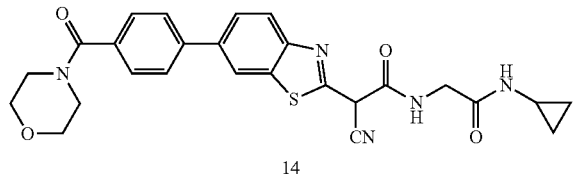

14

Compound 14a. 2-(6-(4-(morpholine-4-carbonyl)phenyl)benzo[d]thiazol-2-yl)acetonitrile To a solution of Compound 1a (51 mg, 0.20 mmol) in dioxane (2 mL) was added (4-(morpholine-4-carbonyl)phenyl)boronic acid (71 mg, 0.30 mmol), phosphoric acid, potassium salt (110 mg, 0.50 mmol), and $PdCl_2(dppf)$ (29 mg, 0.040 mmol). The mixture was degassed with argon and heated at 150° C. for 24 hrs. The reaction mixture was concentrated under reduced pressure and the residue dissolved in DCM/methanol. Silica gel was added and the solvent removed under reduced pressure. The silica loaded residue was added to a silica gel (24 g) column and was eluted with 0-100% EtOAc in hexanes. Fractions containing Compound 14a were collected and concentrated under reduced pressure to generate Compound 14a as a clear liquid (31 mg, 0.080 mmol, 42% yield). MS m/z=364.1 (M+H). $^1$H NMR (500 MHz, $CD_3OD$) δ 8.11 (d, J=8.5 Hz, 1H), 8.09 (d, J=1.9 Hz, 1H), 7.75 (dd, J=1.7, 8.5 Hz, 1H), 7.69 (d, J=8.5 Hz, 2H), 7.53 (d, J=8.5 Hz, 2H), 4.27 (s, 2H), 3.44-3.95 (m, 8H).

Compound 14b. ethyl 2-(2-cyano-2-(6-(4-(morpholine-4-carbonyl)phenyl)benzo[d]thiazol-2-yl)acetamido)acetate To a stirred solution of Compound 14a (31 mg, 0.080 mmol) in THF (2 mL) at 0° C. was added 60% sodium hydride in mineral oil (60%, 4.0 mg, 0.10 mmol). After 20 min, ethyl 2-isocyanatoacetate (0.010 mL, 0.10 mmol) was added and the reaction mixture was allowed to warm to RT, stirred for 1 hr, then heated to 60° C. for 4 hrs. The reaction mixture was concentrated in vacuo and the residue diluted with EtOAc. The organic layer was washed with saturated $NH_4Cl$ solution. The organic layer was separated, dried over $MgSO_4$, filtered and concentrated in vacuo. The residue was added to a silica gel (12 g) column and was eluted with 0-100% EtOAc in hexanes. Fractions containing Compound 14b were collected and concentrated under reduced pressure to yield a yellow solid (15 mg, 0.030 mmol, 37% yield). MS m/z=493.1 (M+H). $^1$H NMR (500 MHz, $CD_3OD$) δ 7.77 (d, J=1.4 Hz, 1H), 7.70 (d, J=8.3 Hz, 1H), 7.61 (d, J=8.3 Hz, 2H), 7.58 (dd, J=1.7, 8.5 Hz, 2H), 7.38 (d, J=8.5 Hz, 2H), 6.28 (t, J=5.5 Hz, 1H), 4.26 (q, J=7.2 Hz, 2H), 3.42-3.93 (m, 10H), 1.26 (t, J=7.2 Hz, 3H).

Compound 14c. 2-(2-cyano-2-(6-(4-(morpholine-4-carbonyl)phenyl)benzo[d]thiazol-2-yl)acetamido)acetic Acid To a solution of Compound 14b (15 mg, 0.030 mmol) in MeOH (1 mL) was added lithium hydroxide monohydrate (2.5 mg, 0.060 mmol) in 1 mL water. The reaction was stirred at ambient temperature for 16 hrs. The reaction mixture was concentrated in vacuo and diluted with EtOAc/THF. The organic layer was washed with 0.1 M HCl. The organic layer was separated, dried over $MgSO_4$, filtered and concentrated in vacuo to give Compound 14c (15 mg, 0.030 mmol, 100% yield) as a light brown solid. MS m/z=465.1 (M+H). $^1$H NMR (500 MHz, THF-d8) δ 7.86 (d, J=1.5 Hz, 1H), 7.66 (d, J=8.3 Hz, 1H), 7.59 (dd, J=1.9, 8.3 Hz, 1H), 7.52 (d, J=8.5 Hz, 2H), 7.39 (d, J=8.3 Hz, 2H), 7.01 (t, J=5.8 Hz, 1H), 3.46-3.48 (m, 8H), 3.42 (d, J=5.0 Hz, 2H).

Example 14. 2-cyano-N-(2-(cyclopropylamino)-2-oxoethyl)-2-(6-(4-(morpholine-4-carbonyl)phenyl)benzo[d]thiazol-2-yl)acetamide To a stirred solution of Compound 14c (15 mg, 0.030 mmol) and cyclopropylamine (2.8 mg, 0.050 mmol) in tetrahydrofuran (2 mL) was added PyBOP (22 mg, 0.040 mmol) and Hunig's base (0.020 mL, 0.10 mmol). The reaction mixture was stirred at ambient temperature for 2 hrs. The reaction mixture was concentrated in vacuo and diluted with EtOAc. The organic layer was washed with 0.1 M HCl. The organic layer was separated, dried over $MgSO_4$, filtered and concentrated in vacuo. The residue was purified via preparative LC/MS with the following conditions: Column: XBridge C18, 19×200 mm, 5 m particles; Mobile Phase A: 5:95 acetonitrile: water with 0.1% trifluoroacetic acid; Mobile Phase B: 95:5 acetonitrile: water with 0.1% trifluoroacetic acid; Gradient: 10-45% B over 20 minutes, then a 5 minute hold at 100% B; Flow: 20 mL/min. Fractions containing Example 14 were combined and dried via centrifugal evaporation. The yield of Example 14 was 5.0 mg (31% yield). The estimated purity by LCMS analysis was 97%, HPLC method A, RT=1.16 min, MS m/z=504.2 (M+H). 1H NMR (500 MHz, DMSO-d6) δ 8.15 (s, 1H), 7.99 (s, 1H), 7.71-7.76 (m, 3H), 7.56 (d, J=8.2 Hz, 1H), 7.50 (d, J=7.9H, 2H), 7.37 (br s, 1H), 3.68-3.74 (m, 2H), 3.09-3.16 (m, 2H), 2.62 (br s, 1H), 2.52-2.55 (m, 2H), 1.79-1.85 (m, 2H), 0.57-0.63 (m, 2H), 0.41 (br s, 2H). EL $IC_{50}$=62 nM.

The following Examples ("Ex") 15 to 20, were prepared by the general procedures described for Example 14.

| Ex # | Structure | Name | NMR | LC/MS RT (min) method M + H | EL IC$_{50}$ (nM) |
|---|---|---|---|---|---|
| 15 | 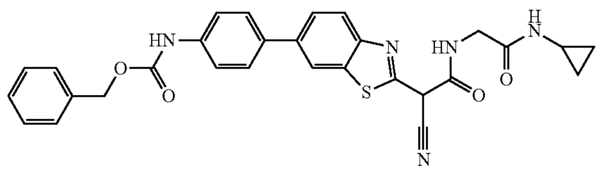 [SMILES: N#CC(C(=O)NCC(=O)NC1CC1)c1nc2ccc(-c3ccc(NC(=O)OCc4ccccc4)cc3)cc2s1] | benzyl N-(4-{2-[cyano ({[(cyclopropyl-carbamoyl) methyl]} carbamoyl) methyl]-1,3-benzothiazol-6-yl}phenyl) carbamate | 1H NMR (500 MHz, DMSO-d6) d 9.89 (s, 1H), 8.06 (s, 1H), 7.98 (s, 1H), 7.58-7.67 (m, 3H), 7.55 (d, J = 8.5 Hz, 2H), 7.51 (d, J = 8.5 H, 1H), 7.38-7.44 (m, 4H), 7.30-7.37 (m, 2H), 5.16 (s, 2H), 3.71 (d, J = 5.2 Hz, 2H), 2.62 (br s, 1H), 0.59-0.63 (m, 2H), 0.41 (br s, 2H) | 1.71 A 540.2 | 1.4 |
| 16 | 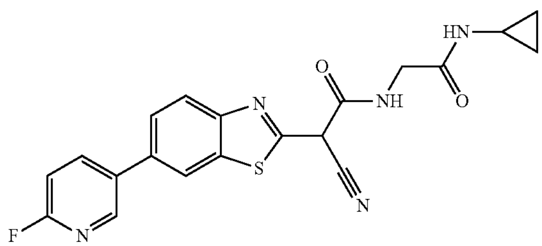 [SMILES: N#CC(C(=O)NCC(=O)NC1CC1)c1nc2ccc(-c3ccc(F)nc3)cc2s1] | 2-cyano-N-[(cyclopropyl-carbamoyl) methyl]-2-[6-(6-fluoropyridin-3-yl)-1,3-benzothiazol-2-yl] acetamide | 1H NMR (500 MHz, DMSO-d6) d 8.55 (s, 1H), 8.28 (t, J = 7.9 Hz, 1H), 8.16 (s, 1H), 7.98 (s, 1H), 7.73 (d, J = 8.2 Hz, 1H), 7.55 (d, J = 8.6 Hz, 1H), 7.37 (br s, 1H), 7.29 (d, J = 8.2 Hz, 2H), 3.71 (d, J = 5.2 Hz, 2H), 2.58-2.66 (m, 1H), 0.59-0.63 (m, 2H), 0.41 (br s, 2H) | 1.26 A 410.2 | 172 |
| 17 | 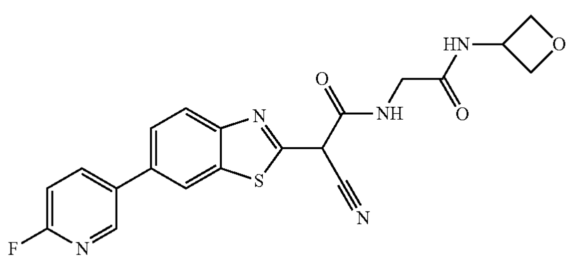 [SMILES: N#CC(C(=O)NCC(=O)NC1COC1)c1nc2ccc(-c3ccc(F)nc3)cc2s1] | 2-cyano-2-[6-(6-fluoropyridin-3-yl)-1,3-benzothiazol-2-yl]-N-{[(oxetan-3-yl)carbamoyl] methyl} acetamide | 1H NMR (500 MHz, DMSO-d6) d 12.84 (s, 1H), 8.66 (d, J = 6.8 Hz, 1H), 8.57 (d, J = 2.4 Hz, 1H), 8.30 (dt, J = 2.4, 8.3 Hz, 1H), 8.18 (s, 1H), 7.74 (d, J = 8.1 Hz, 1H), 7.57 (d, J = 8.6 Hz, 1H), 7.44 (br s, 1H), 7.30 (dd, J = 2.9, 8.6 Hz, 1H), 4.78-4.87 (m, 1H), 4.72 (t, J = 7.3 Hz, 2H), 4.46 (t, J = 6.4 Hz, 2H), 3.80 (d, J = 5.7 Hz, 2H) | 1.18 A 426.1 | 67 |
| 18 | 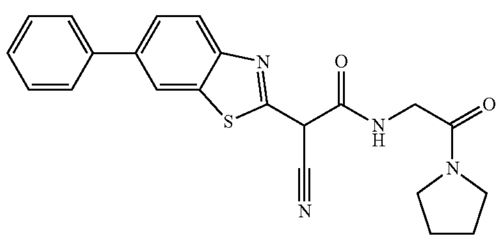 [SMILES: N#CC(C(=O)NCC(=O)N1CCCC1)c1nc2ccc(-c3ccccc3)cc2s1] | 2-cyano-N-[2-oxo-2-(pyrrolidin-1-yl)ethyl]-2-(6-phenyl-1,3-benzothiazol-2-yl)acetamide | 1H NMR (500 MHz, DMSO-d6) d 12.82 (s, 1H), 8.13 (d, J = 1.2 Hz, 1H), 7.66-7.71 (m, 3H), 7.55 (d, J = 8.5 Hz, 1H), 7.40-7.49 (m, 2H), 7.37 (t, J = 7.4 Hz, 1H), 7.18 (t, J = 5.0 Hz, 1H), 3.95 (d, J = 5.0 Hz, 2H), 3.43 (t, J = 6.9 Hz, 2H), 3.33 (t, J = 6.9 Hz, 2H), 1.91 (quart, J = 6.6 Hz, 2H), 1.79 (quart, J = 6.9 Hz, 2H) | 3.62 E 405.1 | 1320 |
| 19 | 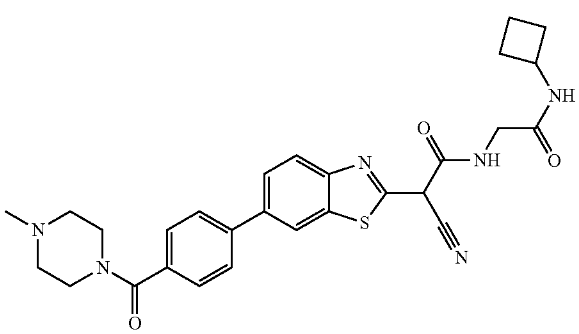 [SMILES: CN1CCN(C(=O)c2ccc(-c3ccc4nc(C(C#N)C(=O)NCC(=O)NC5CCC5)sc4c3)cc2)CC1] | 2-cyano-N-[(cyclobutyl-carbamoyl) methyl]-2-{6-[4-(4-methyl-piperazine-1-carbonyl) phenyl]-1,3-benzothiazol-2-yl} acetamide | 1H NMR (500 MHz, CD3OD) d 7.96 (s, 1H), 7.76 (m, 3H), 7.69 (d, J = 8.5 Hz, 1H), 7.58 (m, 3H), 7.52 (d, J = 8.5 Hz, 1H), 4.33 (quart, J = 8.3 Hz, 1H), 3.91 (s, 2H), 3.47 (br s, 4H), 3.35 (s, 3H), 2.97 (s, 4H), 2.23-2.31 (m, 2H), 1.97-2.05 (m, 2H), 1.71-1.76 (m, 2H) | 2.51 E 531.2 | 3140 |

| Ex # | Structure | Name | NMR | LC/MS RT (min) method M + H | EL IC$_{50}$ (nM) |
|---|---|---|---|---|---|
| 20 | 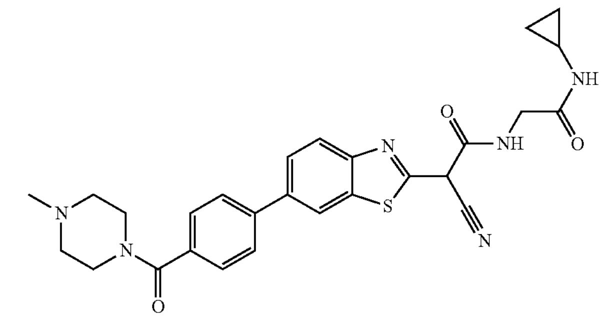 [SMILES: CN1CCN(C(=O)c2ccc(-c3ccc4nc(C(C#N)C(=O)NCC(=O)NC5CC5)sc4c3)cc2)CC1] | 2-cyano-N-[(cyclopropyl-carbamoyl)methyl]-2-{6-[4-(4-methyl-piperazine-1-carbonyl)phenyl]-1,3-benzothiazol-2-yl} acetamide | 1H NMR (500 MHz, CD3OD) d 7.96 (d, J = 1.7 Hz, 1H), 7.73-7.79 (m, 3H), 7.69 (dd, J = 1.7, 8.5 Hz, 1H), 7.56-7.59 (m, 3H), 7.52 (d, J = 8.5 Hz, 1H), 3.90 (s, 2H), 3.48 (br s, 4H), 3.35 (s, 3H), 2.97 (s, 4H), 2.66-2.71 (m, 1H), 0.70-0.74 (m, 2H), 0.52-0.56 (m, 2H) | 2.26 E 517.1 | 130 |

Example 21. 2-cyano-N-(2-(cyclopropylamino)-2-oxoethyl)-2-(6-phenylthiazolo[4,5-b]pyridin-2-yl) acetamide

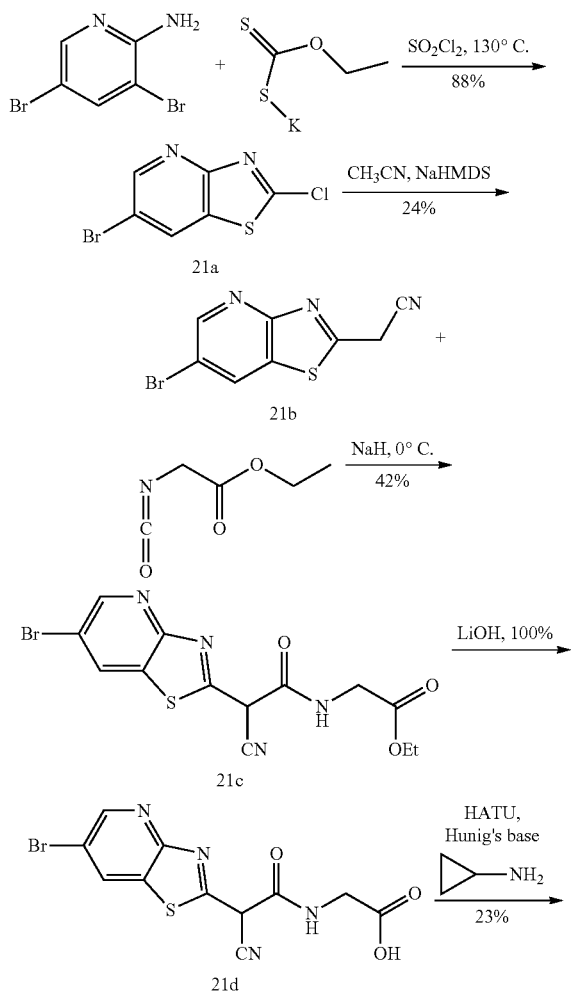

Compound 21a.
6-bromo-2-chlorothiazolo[4,5-b]pyridine

A solution of 3,5-dibromopyridine-2-amine (5.0 g, 20 mmol) and ethylxanthic acid potassium salt (7.6 g, 48 mmol) in DMF (25 mL) was heated to 130° C. for 16 hrs. The reaction was allowed to cool to RT. 1 N HCl (150 mL) was added and the reaction mixture was stirred for 1 hr. A precipitate formed and was collected by filtration. The light yellow solid was suspended in DCM (25 mL), sulfuryl chloride (9.7 mL, 120 mmol) was added slowly. After 2 hrs, the reaction mixture was cooled to 0° C. and water was added very carefully. The precipitate that formed was collected to give Compound 21a (5.0 g, 18 mmol, 88% yield) as a light yellow solid, HCl salt. MS m/z=250.8 (M+H). 1H NMR (500 MHz, DMSO-d6) δ 8.91 (s, 1H), 8.82 (s, 1H).

Compound 21b. 2-(6-bromothiazolo[4,5-b]pyridin-2-yl)acetonitrile 3.4 g of Compound 21a, HCl salt was suspended in EtOAc and washed with 1 N NaOH. The organic layer was separated, dried over MgSO$_4$, filtered and concentrated in vacuo to give 2.6 g of Compound 21a, free base.

To a stirred solution of Compound 21a, free base, (2.6 g, 0.010 mol) and acetonitrile (1.6 mL, 31 mmol) in THF (50 mL) at 0° C. was added 1 M sodium bis(trimethylsilyl)amide in THF (31 mL, 31 mmol). The reaction mixture was allowed to warm to RT and stirred for 1 hr. The reaction mixture was concentrated in vacuo and diluted with EtOAc. The organic layer was washed with water. The organic layer was separated, dried over MgSO$_4$, filtered and concentrated in vacuo. The residue was triturated with EtOAc, to generate Compound 21b (630 mg, 2.5 mmol, 24%) as a dark brown solid. MS m/z=255.8 (M+H).

Compound 21c. ethyl 2-(2-(6-bromothiazolo[4,5-b]pyridin-2-yl)-2-cyanoacetamido)acetate To a stirred solution of Compound 21b (630 mg, 2.5 mmol) in THF (15 mL) at 0° C. was added 60% sodium hydride in mineral oil (120 mg, 3.0 mmol). After 20 min, ethyl 2-isocyanatoacetate (0.40 mL, 3.2 mmol) was added and the reaction was allowed to warm to RT and stirred for 1 hr. The reaction mixture was concentrated in vacuo and diluted with EtOAc. The organic layer was washed with saturated NH$_4$Cl solution (pH=7). A precipitate formed which was collected by filtration to yield 250 mg of Compound 21c as a dark brown solid. Additional Compound 21c was obtained from the organic layer which was dried over MgSO$_4$, filtered and concentrated in vacuo. The filtrate residue was added to a silica gel (80 g) column and was eluted with 20-100% EtOAc in hexanes. Fractions containing additional Compound 21c were collected and concentrated under reduced pressure to yield a total of 410 mg, 1.1 mmol, 42% yield Compound 21c as a yellow solid. MS m/z=384.9 (M+H). 1H NMR (500 MHz, DMSO-d6) δ 8.46 (br s, 1H), 8.37 (s, 1H), 8.35 (s, 1H), 6.51 (t, J=5.5 Hz, 1H), 4.10 (q, J=7.2 Hz, 2H), 3.88 (d, J=5.2 Hz, 2H), 1.19 (t, J=7.2 Hz, 3H).

Compound 21d. 2-(2-(6-bromothiazolo[4,5-b]pyridin-2-yl)-2-cyanoacetamido)acetic Acid Compound 21c (51 mg, 0.13 mmol) was dissolved in THF (10 ml) and lithium hydroxide monohydrate (14 mg, 0.30 mmol) in water was added and the reaction mixture was stirred at RT for 2 hrs. The reaction mixture was concentrated under reduced pressure to give Compound 21d (47 mg, 0.13 mmol, 100% yield) as a tan solid, Li salt. MS m/z=354.9 (M+H).

Compound 21e. 2-(6-bromothiazolo[4,5-b]pyridin-2-yl)-2-cyano-N-(2-(cyclopropylamino)-2-oxoethyl)acetamide Compound 21d (47 mg, 0.13 mmol) and cyclopropylamine (16 mg, 0.30 mmol) were dissolved in DMF (5 mL). HATU (110 mg, 0.28 mmol) and Hunig's Base (0.070 mL, 0.40 mmol) were added, and the reaction mixture was stirred at ambient temperature for 2 hrs. The reaction mixture was concentrated in vacuo and the residue diluted with EtOAc/THF. The organic layer was washed with saturated NH$_4$Cl (pH=7). The organic layer was separated, dried over MgSO$_4$, filtered and concentrated in vacuo. The residue was purified by prep HPLC (Phenomenex Luna AXIA 5μ C18 30×100 mm column; detection at 220 nm; flow rate=40 mL/min; continuous gradient from 0% B to 100% B over 12 min+3 min hold time at 100% B, where A=90:10:0.1 H$_2$O: MeOH:TFA and B=90:10:0.1 MeOH:H$_2$O:TFA) and concentrated under reduced pressure. The resulting solid was dissolved in THF/EtOAc and washed with saturated NaHCO$_3$ solution. The organic layer was dried over MgSO$_4$, filtered and concentrated in vacuo to give Compound 21e (13 mg, 0.030 mmol, 23% yield) as a light yellow solid. MS m/z=395.9 (M+H). 1H NMR (500 MHz, THF-d8) δ 8.17 (s, 1H), 8.02 (s, 1H), 3.58 (d, J=6.6 Hz, 2H), 2.71 (m, 1H), 0.57 (br s, 2H), 0.44 (br s, 2H).

Example 21. 2-cyano-N-(2-(cyclopropylamino)-2-oxoethyl)-2-(6-phenylthiazolo[4,5-b]pyridin-2-yl)acetamide To a mixture of Compound 21e (13 mg, 0.030 mmol), phenylboronic acid (4.8 mg, 0.040 mmol), tripotassiumphosphate (21 mg, 0.10 mmol) and 2nd generation XPHOS precatalyst (2.6 mg, 3.3 μmol) was added dioxane (5 mL) and water (2 mL). The mixture was degassed with argon and heated at 90° C. for 1 hr. The reaction mixture was allowed to cool to RT and concentrated in vacuo. The residue was purified via preparative LC/MS with the following conditions: Column: XBridge C18, 19×200 mm, m particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 20 minutes, then a 5 minute hold at 100% B; Flow: 20 mL/min. Fractions containing Example 21 were combined and dried via centrifugal evaporation. The yield of the Compound 21 was 5.6 mg (43% yield). The estimated purity by LCMS analysis was 96%, HPLC method A, RT=1.32 min, MS m/z=392.4 (M+H). 1H NMR (500 MHz, DMSO-d6) δ 8.63 (s, 1H), 8.48 (s, 1H), 7.97 (s, 1H), 7.76 (d, J=7.6 Hz, 2H), 7.51 (t, J=7.3 Hz, 2H), 7.42 (t, J=7.0 Hz, 1H), 3.74 (d, J=4.9 Hz, 2H), 2.62-2.66 (m, 1H), 0.61-0.65 (m, 2H), 0.42-0.45 (m, 2H). EL IC$_{50}$=13 nM.

The following Example 22 to 25, were prepared by the general procedures described for Example 21.

| Ex # | Structure | Name | NMR | LC/MS RT (min) method M + H | EL IC$_{50}$ (nM) |
|---|---|---|---|---|---|
| 22 | 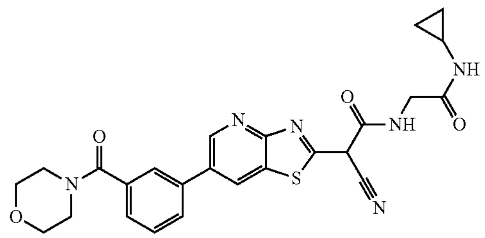 | 2-cyano-N-[(cyclopropyl-carbamoyl)methyl]-2-{6-[3-(morpholine-4-carbonyl)phenyl]-[1,3]thiazolo[4,5-b]pyridin-2-yl}acetamide | 1H NMR (500 MHz, DMSO-d6) d 8.70 (s, 1H), 8.52 (s, 1H), 7.99 (d, J = 3.7 Hz, 1H), 7.85 (d, J = 7.6 Hz, 1H), 7.78 (s, 1H), 7.59 (t, J = 7.6 Hz, 1H), 7.45 (d, J = 7.6 Hz, 1H), 7.21 (br s, 1H), 3.74 (d, J = 5.2 Hz, 2H), 3.44-3.71 (m, 8H), 2.61-2.66 (m, 1H), 0.61-0.65 (m, 2H), 0.43 (br s, 2H) | 1.07 A 505.3 | 22 |
| 23 | 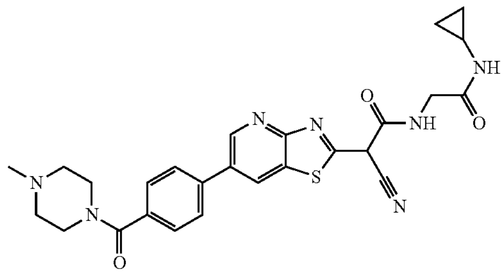 [SMILES: CN1CCN(C(=O)c2ccc(-c3cnc4nc(C(C#N)C(=O)NCC(=O)NC5CC5)sc4c3)cc2)CC1] | 2-cyano-N-[(cyclopropyl-carbamoyl)methyl]-2-{6-[4-(4-methylpiperazine-1-carbonyl)phenyl]-[1,3]thiazolo[4,5-b]pyridin-2-yl}acetamide | 1H NMR (500MHz, DMSO-d6) d 8.68 (s, 1H), 8.54 (s, 1H), 7.99 (d, J = 3.7 Hz, 1H), 7.87 (d, J = 8.2 Hz, 2H), 7.59 (d, J = 8.2 Hz, 2H), 7.21 (br s, 1H), 3.74 (d, J = 5.2 Hz, 2H), 3.41-3.59 (m, 4H), 3.18-3.38 (m, 4H), 2.84 (s, 3H), 2.61-2.66 (m, 1H), 0.61-0.65 (m, 2H), 0.41-0.44 (m, 2H) | 0.97 A 518.4 | 33 |
| 24 | 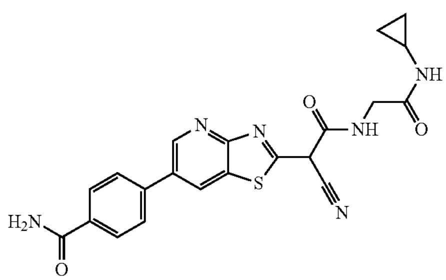 [SMILES: N#CC(C(=O)NCC(=O)NC1CC1)c1nc2ncc(-c3ccc(C(N)=O)cc3)cc2s1] | 4-{2-[cyano({[(cyclopropyl-carbamoyl)methyl]carbamoyl})methyl]-[1,3]thiazolo[4,5-b]pyridin-6-yl}benzamide | 1H NMR (500 MHz, DMSO-d6) d 8.70 (s, 1H), 8.54 (s, 1H), 8.09 (s, 1H), 7.99 (d, J = 8.2 Hz, 2H), 7.85 (d, J = 8.2 Hz, 2H), 7.41 (s, 1H), 7.22 (br s, 1H), 3.74 (d, J = 5.2 Hz, 2H), 2.61-2.66 (m, 1H), 0.61-0.65 (m, 2H), 0.41-0.44 (m, 2H) | 0.89 A 435.4 | 31 |
| 25 | 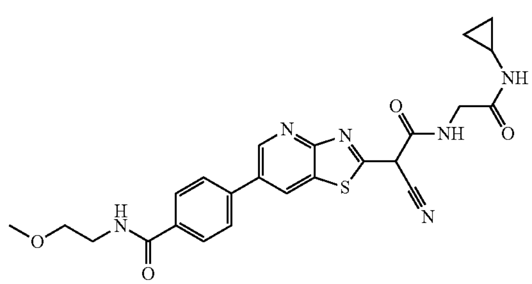 [SMILES: COCCNC(=O)c1ccc(-c2cnc3nc(C(C#N)C(=O)NCC(=O)NC4CC4)sc3c2)cc1] | 4-{2-[cyano({[(cyclopropyl-carbamoyl)methyl]carbamoyl})methyl]-[1,3]thiazolo[4,5-b]pyridin-6-yl}-N-(2-methoxyethyl)benzamide | 1H NMR (500 MHz, DMSO-d6) d 8.68 (s, 1H), 8.61-8.63 (m, 2H), 8.52 (s, 1H), 8.01 (d, J = 3.4 Hz, 1H), 7.96 (d, J = 8.2 Hz, 2H), 7.84 (d, J = 7.9 Hz, 2H), 7.23 (br s, 1H), 3.63-3.72 (m, 4H), 3.45-3.51 (m, 2H), 3.28 (s, 3H), 2.60-2.66 (m, 1H), 0.61-0.65 (m, 2H), 0.42 (br s, 2H) | 1.02 A 493.4 | 40 |

Example 26. 3-{2-[cyano({[(cyclopropylcarbamoyl)methyl]carbamoyl})methyl]-6-fluoro-1,3-benzothiazol-5-yl}benzamide

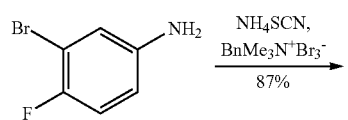

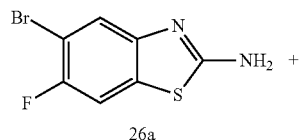

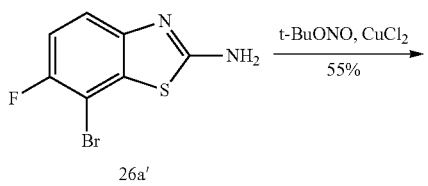

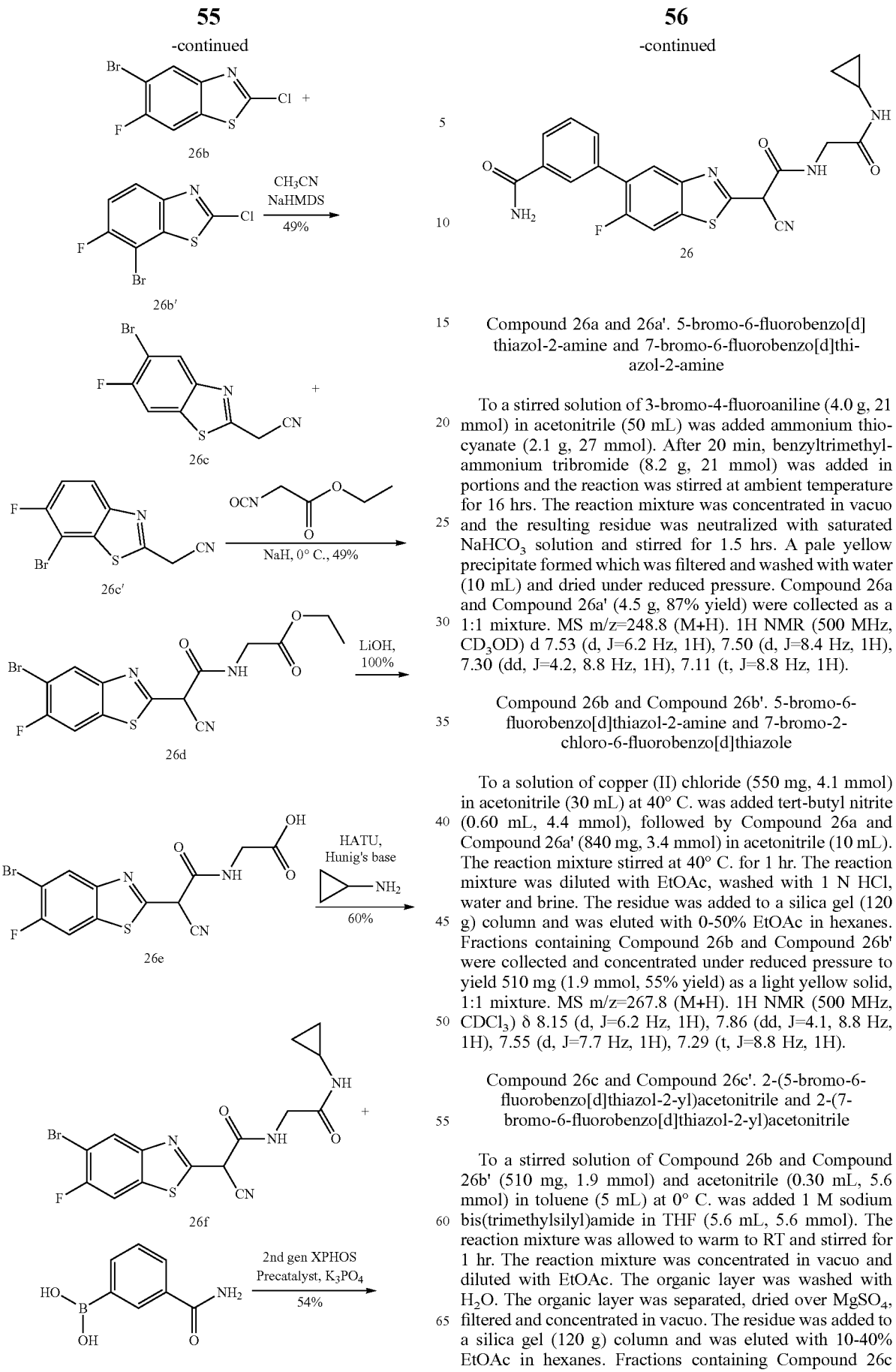

Compound 26a and 26a'. 5-bromo-6-fluorobenzo[d]thiazol-2-amine and 7-bromo-6-fluorobenzo[d]thiazol-2-amine To a stirred solution of 3-bromo-4-fluoroaniline (4.0 g, 21 mmol) in acetonitrile (50 mL) was added ammonium thiocyanate (2.1 g, 27 mmol). After 20 min, benzyltrimethylammonium tribromide (8.2 g, 21 mmol) was added in portions and the reaction was stirred at ambient temperature for 16 hrs. The reaction mixture was concentrated in vacuo and the resulting residue was neutralized with saturated $NaHCO_3$ solution and stirred for 1.5 hrs. A pale yellow precipitate formed which was filtered and washed with water (10 mL) and dried under reduced pressure. Compound 26a and Compound 26a' (4.5 g, 87% yield) were collected as a 1:1 mixture. MS m/z=248.8 (M+H). 1H NMR (500 MHz, $CD_3OD$) d 7.53 (d, J=6.2 Hz, 1H), 7.50 (d, J=8.4 Hz, 1H), 7.30 (dd, J=4.2, 8.8 Hz, 1H), 7.11 (t, J=8.8 Hz, 1H).

Compound 26b and Compound 26b'. 5-bromo-6-fluorobenzo[d]thiazol-2-amine and 7-bromo-2-chloro-6-fluorobenzo[d]thiazole To a solution of copper (II) chloride (550 mg, 4.1 mmol) in acetonitrile (30 mL) at 40° C. was added tert-butyl nitrite (0.60 mL, 4.4 mmol), followed by Compound 26a and Compound 26a' (840 mg, 3.4 mmol) in acetonitrile (10 mL). The reaction mixture stirred at 40° C. for 1 hr. The reaction mixture was diluted with EtOAc, washed with 1 N HCl, water and brine. The residue was added to a silica gel (120 g) column and was eluted with 0-50% EtOAc in hexanes. Fractions containing Compound 26b and Compound 26b' were collected and concentrated under reduced pressure to yield 510 mg (1.9 mmol, 55% yield) as a light yellow solid, 1:1 mixture. MS m/z=267.8 (M+H). 1H NMR (500 MHz, $CDCl_3$) δ 8.15 (d, J=6.2 Hz, 1H), 7.86 (dd, J=4.1, 8.8 Hz, 1H), 7.55 (d, J=7.7 Hz, 1H), 7.29 (t, J=8.8 Hz, 1H).

Compound 26c and Compound 26c'. 2-(5-bromo-6-fluorobenzo[d]thiazol-2-yl)acetonitrile and 2-(7-bromo-6-fluorobenzo[d]thiazol-2-yl)acetonitrile To a stirred solution of Compound 26b and Compound 26b' (510 mg, 1.9 mmol) and acetonitrile (0.30 mL, 5.6 mmol) in toluene (5 mL) at 0° C. was added 1 M sodium bis(trimethylsilyl)amide in THF (5.6 mL, 5.6 mmol). The reaction mixture was allowed to warm to RT and stirred for 1 hr. The reaction mixture was concentrated in vacuo and diluted with EtOAc. The organic layer was washed with $H_2O$. The organic layer was separated, dried over $MgSO_4$, filtered and concentrated in vacuo. The residue was added to a silica gel (120 g) column and was eluted with 10-40% EtOAc in hexanes. Fractions containing Compound 26c were collected and concentrated under reduced pressure yielding 250 mg (0.9 mmol, 49% yield) as a light yellow solid, contains 20% of Compound 26c'. MS m/z=272.8 (M+H). 1H NMR (500 MHz, CDCl$_3$) δ 8.24 (d, J=6.1 Hz, 1H), 7.65 (d, J=7.7 Hz, 1H), 4.23 (s, 2H).

Compound 26d. ethyl 2-(2-(5-bromo-6-fluorobenzo[d]thiazol-2-yl)-2-cyanoacetamido)acetate To a stirred solution of Compound 26c (250 mg, 0.90 mmol) in THF (8 mL) at 0° C. was added 60% sodium hydride in mineral oil (44 mg, 1.1 mmol). After 20 min, ethyl 2-isocyanatoacetate (0.10 mL, 1.2 mmol) was added and the reaction was allowed to warm to RT and stirred for 1 hr. The reaction mixture quenched with 1 N HCl and diluted with EtOAc. The organic layer was separated, dried over MgSO$_4$, filtered and concentrated in vacuo. The resulting solid was triturated with DCM to generate Compound 26d (180 mg, 0.45 mmol, 49% yield) as a tan solid. The undesired isomer was left in the filtrate. MS m/z=401.9 (M+H). 1H NMR (500 MHz, DMSO-d6) δ 7.94 (d, J=8.3 Hz, 1H), 7.79 (br s, 1H), 7.65 (d, J=6.1 Hz, 1H), 4.11 (q, J=7.2 Hz, 2H), 3.88 (d, J=5.8 Hz, 2H), 1.20 (t, J=7.2 Hz, 3H).

Compound 26e. 2-(2-(5-bromo-6-fluorobenzo[d]thiazol-2-yl)-2-cyanoacetamido)acetic Acid Compound 26d (180 mg, 0.45 mmol) was dissolved in THF (10 mL) and lithium hydroxide monohydrate (47 mg, 1.1 mmol) in water (1 mL) was added and the reaction mixture was stirred at RT for 2 hrs. The reaction mixture was concentrated under reduced pressure to give Compound 26e (180 mg, 0.45 mmol, 100% yield) as a tan solid, Li salt. MS m/z=373.9 (M+H).

Compound 26f. 2-(5-bromo-6-fluorobenzo[d]thiazol-2-yl)-2-cyano-N-(2-(cyclopropylamino)-2-oxoethyl)acetamide Compound 26d (180 mg, 0.45 mmol) and cyclopropylamine (55 mg, 1.0 mmol) were dissolved in DMF (25 mL). HATU (370 mg, 1.0 mmol) and Hunig's Base (0.25 mL, 1.5 mmol) were added, and the reaction stirred at ambient temperature for 2 hrs. The reaction mixture was concentrated in vacuo and diluted with EtOAc/THF. The organic layer was washed with H$_2$O, separated, dried over MgSO$_4$, filtered and concentrated in vacuo. The residue was triturated with methanol to generate Compound 26f (100 mg, 50% yield) as an off white solid. The filtrate was purified by prep HPLC (Phenomenex Luna AXIA 5μ C18 30×100 mm column; detection at 220 nm; flow rate=40 mL/min; continuous gradient from 0% B to 100% B over 12 min+3 min hold time at 100% B, where A=90:10:0.1 H$_2$O:MeOH:TFA and B=90:10:0.1 MeOH:H$_2$O:TFA) to give additional Compound 26f (20 mg, 10% yield) as a light yellow solid. MS m/z=412.9 (M+H). 1H NMR (500 MHz, DMSO-d6) δ 13.00 (s, 1H), 7.96 (d, J=3.9 Hz, 1H), 7.48 (t, J=5.5 Hz, 1H), 7.38-7.44 (m, 2H), 3.72 (d, J=5.2 Hz, 2H), 2.61-2.66 (m, 1H), 0.60-0.66 (m, 2H), 0.40-0.43 (m, 2H).

Example 26. 3-{2-[cyano({[(cyclopropylcarbamoyl)methyl]carbamoyl})methyl]-6-fluoro-1,3-benzothiazol-5-yl}benzamide To a mixture of Compound 26f (10 mg, 0.02 mmol), (3-carbamoylphenyl)boronic acid (4.8 mg, 0.030 mmol), tripotassiumphosphate (16 mg, 0.070 mmol) and 2nd generation XPHOS precatalyst (1.9 mg, 2.4 μmol) was added dioxane (1.5 mL) and water (0.5 mL). The reaction mixture was degassed with argon and heated at 90° C. for 1 hr. The reaction mixture was concentrated in vacuo and diluted with EtOAc. The organic layer was washed with saturated NH$_4$Cl solution. The organic layer was separated, dried over MgSO$_4$, filtered and concentrated in vacuo. The residue was purified via preparative LC/MS with the following conditions: Column: XBridge C18, 19×200 mm, 5-m particles; Mobile Phase A: 5:95 acetonitrile: water with 0.1% formic acid; Mobile Phase B: 95:5 acetonitrile: water with 0.1% formic acid; Gradient: 5-50% B over 20 minutes, then a 5-minute hold at 100% B; Flow: 20 mL/min. Fractions containing Example 26 were combined and dried via centrifugal evaporation. The yield of Example 26 was 5.9 mg (54% yield). The estimated purity by LCMS analysis was 98%, HPLC method A, RT=1.17 min, MS m/z=452.4 (M+H). 1H NMR (500 MHz, DMSO-d6) δ 8.05-8.12 (m, 2H), 7.92-7.99 (m, 2H), 7.88 (d, J=8.8 Hz, 1H), 7.72 (d, J=7.3 Hz, 1H), 7.60 (t, J=7.6 Hz, 1H), 7.54 (d, J=6.1 Hz, 1H), 7.45 (br s, 1H), 3.74 (d, J=5.2 Hz, 2H), 2.61-2.66 (m, 1H), 0.61-0.65 (m, 2H), 0.43 (br s, 2H). EL IC$_{50}$=21 nM.

The following Examples 27 to 29, were prepared by the general procedures described for Example 26.

| Ex# | Structure | Name | NMR | LC/MS RT (min) method M + H | EL IC$_{50}$ (nM) |
|---|---|---|---|---|---|
| 27 | 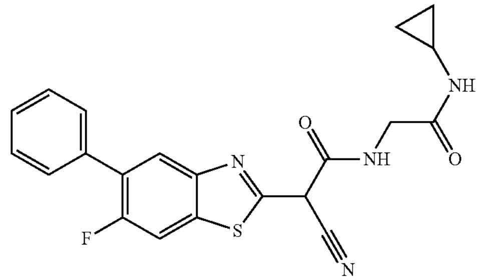 [SMILES: N#CC(C(=O)NCC(=O)NC1CC1)c1nc2cc(-c3ccccc3)c(F)cc2s1] | 2-cyano-N-[(cyclopropylcarbamoyl)methyl]-2-(6-fluoro-5-phenyl-1,3-benzothiazol-2-yl)acetamide | 1H NMR (500 MHz, DMSO-d6) d 7.97 (s, 1H), 7.84 (d, J = 9.8 Hz, 1H), 7.47-7.58 (m, 5H), 7.45 (t, J = 7.0 Hz, 1H), 7.30 (br s, 1H), 3.73 (d, J = 5.2 Hz, 2H), 2.60-2.66 (m, 1H), 0.60-0.65 (m, 2H), 0.43 (br s, 2H) | 1.62 A 408.9 | 13 |

-continued

| Ex# | Structure | Name | NMR | LC/MS RT (min) method M + H | EL IC$_{50}$ (nM) |
|---|---|---|---|---|---|
| 28 | 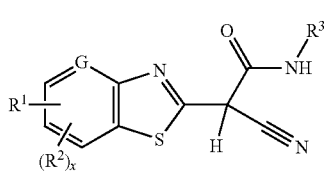 | 4-{2-[cyano ({[(cyclopropyl-carbamoyl) methyl] carbamoyl}) methyl]-6-fluoro-1,3-benzothiazol-5-yl}benzamide | 1H NMR (500 MHz, DMSO-d6) d 8.05 (s, 1H), 8.00 (d, J = 8.4 Hz, 2H), 7.96 (d, J = 6.0 Hz, 1H), 7.89 (d, J = 9.9 Hz, 1H), 7.63 (d, J = 7.0 Hz, 2H), 7.53 (d, J = 5.5 Hz, 1H), 7.43 (s, 1H), 7.35 (br s, 1H), 3.73 (d, J = 5.5 Hz, 2H), 2.61-2.66 (m, 1H), 0.60-0.65 (m, 2H), 0.41-0.44 (m, 2H) | 1.19 B 452.0 | <1 |
| 29 | 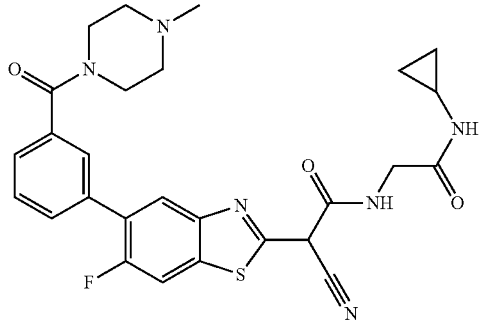 [SMILES: CN1CCN(C(=O)c2cccc(-c3cc4nc(C(C#N)C(=O)NCC(=O)NC5CC5)sc4cc3F)c2)CC1] | 2-cyano-N-[(cyclopropyl-carbamoyl) methyl]-2-{6-fluoro-5-[3-(4-methylpiperazine-1-carbonyl)phenyl]-1,3-benzothiazol-2-yl}acetamide | 1H NMR (500 MHz, DMSO-d6) d 7.99 (s, 1H), 7.86 (d, J = 9.5 Hz, 1H), 7.60-7.72 (m, 6H), 7.49-7.55 (m, 2H), 7.33 (br s, 1H), 3.73 (d, J = 4.6 Hz, 2H), 3.58 (m, 4H), 3.17-3.29 (m, 4H), 2.80 (s, 3H), 2.61-2.65 (m, 1H), 0.59-0.66 (m, 2H), 0.42 (br s, 2H) | 1.20 A 535.4 | 1 |

What is claimed is:

1. A compound of Formula (I):

(I)

or a stereoisomer, a tautomer, or a pharmaceutically acceptable salt or a solvate thereof, wherein:
G is N or C;
$R^1$ is phenyl, a 5- or 6-membered heteroaryl, or a 5- or 6-membered non-aromatic heterocyclyl; wherein the heteroaryl or non-aromatic heterocyclyl each independently comprises one or more carbon atoms and 1 to 4 heteroatoms selected from N, $NR^a$, O, and $S(O)_z$, and the phenyl, heteroaryl or non-aromatic heterocyclyl is each independently substituted with 0, 1, 2, or 3 $R^6$;
$R^2$ is, independently at each occurrence, selected from: halogen, OH, $C_{1-4}$ alkyl, $C_{1-4}$ alkoxy, $C_{1-4}$ haloalkyl, $C_{1-4}$ haloalkoxy, CN, $NR^bR^c$, $NO_2$, $CO_2R^d$, and $CONR^bR^c$;
$R^3$ is —$(CH_2)_y$—$CONR^eR^4$;
$R^e$ is hydrogen, $C_{1-4}$ alkyl, or $C_{3-6}$ carbocyclyl;
$R^4$ is $C_{1-6}$ alkyl substituted with 0, 1, or 2 $R^7$, —$(CH_2)_Q$—$(C_{3-6}$ carbocyclyl substituted with 0, 1, or 2 $R^7$), or —$(CH_2)_Q$-(4- to 6-membered heterocyclyl comprising one or more carbon atoms and 1 to 4 heteroatoms selected from N, $NR^a$, O, and $S(O)_z$, wherein the heterocycle is substituted with 0, 1, or 2 $R^7$;
or alternatively, $R^e$ and $R^4$, taken together with the atoms to which they are attached, form a 5- or 6-membered azacyclyl comprising one or more carbon atoms and 1 to 4 heteroatoms selected from N, $NR^a$, O, and $S(O)_z$, wherein the azacyclyl is substituted with 0, 1, or 2 $R^5$;
$R^6$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NR^fR^g$, OPh, OBn, Ph, and —$CONR^hR^i$; or alternatively, two $R^6$, taken together with the atoms to which they are attached, form a 5- or 6-membered carbocyclyl, heteroaryl or non-aromatic heterocyclyl; wherein the heteroaryl or non-aromatic heterocyclyl each independently comprises one or more carbon atoms and 1 to 4 heteroatoms selected from N, $NR^a$, O, and $S(O)_z$, and the carbocyclyl, heteroaryl or non-aromatic heterocyclyl is each independently substituted with 0, 1, 2, or 3 $R^8$;
$R^5$, $R^7$, $R^8$, and $R^9$ are, independently at each occurrence, selected from: OH, halogen, $C_{1-6}$ alkyl, $C_{1-4}$ alkoxy, $C_{1-4}$ haloalkyl, $C_{1-4}$ haloalkoxy, $NR^jR^k$, OPh, OBn, Ph, and a 5- or 6-membered heteroaryl comprising one or more carbon atoms and 1 to 4 heteroatoms selected from N, $NR^a$ and O;
$R^a$, $R^b$, $R^c$, $R^d$, $R^e$, $R^j$, and $R^k$ are, independently at each occurrence, hydrogen, $C_{1-4}$ alkyl, or $C_{3-6}$ carbocyclyl;
$R^f$ and $R^g$ are independently hydrogen, $C_{1-4}$ alkyl, $C_{3-6}$ carbocyclyl, $CO_2R^m$, or $CONR^nR^p$;
$R^h$ and $R^i$ are independently hydrogen, $C_{1-4}$ alkyl, $C_{3-6}$ carbocyclyl, $C_{1-4}$ alkoxy, $C_{1-4}$ haloalkyl, $C_{1-4}$ haloalkoxy; or alternatively, $R^h$ and $R^i$, taken together with the atoms to which they are attached, form a 5- or 6-membered azacyclyl comprising one or more carbon atoms and 1 to 4 heteroatoms selected from N, NR$^a$, O, and S(O)$_Z$, wherein the azacyclyl is substituted with 0, 1, or 2 R$^9$;

R$^m$, R$^n$, and R$^p$ are independently hydrogen, C$_{1-4}$ alkyl, C$_{3-6}$ carbocyclyl, C$_{1-4}$ alkoxy, C$_{1-4}$ haloalkyl, C$_{1-4}$ haloalkoxy, aryl, arylalkyl, or a 5- or 6-membered heteroaryl comprising one or more carbon atoms and 1 to 4 heteroatoms selected from N, NR$^a$ and O;

X is 0, 1, 2, or 3;
Y is 1, 2, or 3;
Z is, independently at each occurrence, 0, 1, or 2; and
Q is, independently at each occurrence, 0, 1, 2 or 3.

2. The compound according to claim 1, wherein the compound is represented by Formula (IIa) or (IIb):

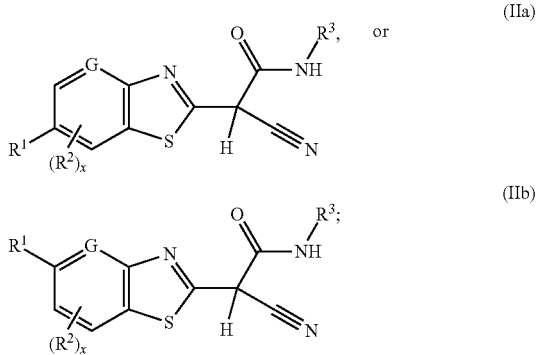

wherein:
G is N or C;
m is 0, 1, or 2; and
R$^2$ is, independently at each occurrence, selected from: halogen, C$_{1-4}$ alkyl, C$_{1-4}$ alkoxy, C$_{1-4}$ haloalkyl, and C$_{1-4}$ haloalkoxy.

3. The compound according to claim 1, wherein R$^1$ is phenyl, pyridinyl, pyrrolidinonyl, or pyridinonyl, each of which is independently substituted with 0, 1, 2, or 3 R$^6$.

4. The compound according to claim 1, wherein
R$^3$ is —(CH$_2$)$_Y$—CONH(C$_{3-6}$ carbocyclyl substituted with 0, 1, or 2 R$^7$), —(CH$_2$)$_Y$—CONH(4- to 6-membered heterocyclyl substituted with 0, 1, or 2 R$^7$), or —(CH$_2$)$_Y$—CONR$^e$R$^4$;
Y is 1 or 2; and
R$^e$ and R$^4$, taken together with the atoms to which they are attached, form a 5- or 6-membered azacyclyl, which is substituted with 0, 1, or 2 R$^5$.

5. The compound according to claim 4, wherein
R$^3$ is —(CH$_2$)$_Y$—CONH(C$_{3-6}$ cycloalkyl substituted with 0, 1, or 2 R$^7$), —(CH$_2$)$_Y$—CONH(4- to 6-membered heterocycloalkyl substituted with 0, 1, or 2 R$^7$), or —(CH$_2$)$_Y$—CONR$^e$R$^4$;
Y is 1; and
R$^e$ and R$^4$, taken together with the atoms to which they are attached, form azetidinyl, pyrrolidinyl, piperidinyl, morpholinyl, or piperazinyl, each of which is substituted with 0, 1, or 2 R$^5$.

6. The compound according to claim 1, wherein
R$^6$ is not present or R$^6$ is OH, halogen, C$_{1-6}$ alkyl, C$_{1-4}$ alkoxy, C$_{1-4}$ haloalkyl, NH$_2$, NHR$^g$, and —CONR$^h$R$^i$;
R$^g$ is C$_{1-4}$ alkyl, CO$_2$R$^m$, CONHR$^p$, or CONR$^n$R$^p$;
R$^h$ and R$^i$ are independently hydrogen, C$_{1-4}$ alkyl, C$_{1-4}$ alkoxy, C$_{1-4}$ haloalkyl, C$_{1-4}$ haloalkoxy; or alternatively, R$^h$ and R$^i$, taken together with the atoms to which they are attached, form a 5- or 6-membered azacyclyl comprising one or more carbon atoms and 1 to 4 heteroatoms selected from N, NR$^a$, O, and S(O)$_Z$, wherein the azacyclyl is substituted with 0, 1, or 2 R$^9$; and R$^m$, R$^n$, and R$^p$ are independently C$_{1-4}$ alkyl, C$_{1-4}$ alkoxy, C$_{1-4}$ haloalkyl, or C$_{1-4}$ haloalkoxy.

7. The compound according to claim 5, wherein R$^3$ is —(CH$_2$)$_Y$—CONHR$^4$; and R$^4$ is cyclopropyl, cyclobutyl, cyclopentyl, oxetanyl, tetrahydrofuranyl, tetrahydropyranyl, azetidinyl, pyrrolidinyl, piperidinyl, morpholinyl, or piperazinyl, each of which is substituted with 0, 1, or 2 R$^7$.

8. The compound according to claim 6, wherein R$^h$ and R$^i$ are, taken together with the atoms to which they are attached, form azetidinyl, pyrrolidinyl, piperidinyl, morpholinyl, or piperazinyl, each of which is independently substituted with 0, 1, or 2 R$^9$.

9. The compound according to claim 1, wherein the compound is represented by Formula (IIIa) or (IIIb):

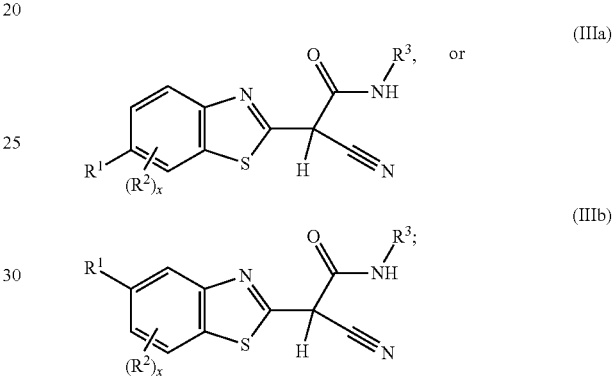

wherein:
R$^1$ is phenyl, pyridinyl, pyrrolidinonyl, or pyridinonyl; wherein the phenyl, pyridinyl, or pyridinonyl is each independently substituted with 0 or 1 R$^6$;
R$^2$ is, independently at each occurrence, selected from: halogen, OH, C$_{1-4}$ alkyl, C$_{1-4}$ alkoxy, C$_{1-4}$ haloalkyl, C$_{1-4}$ haloalkoxy, CN, NH$_2$, NH(C$_{1-4}$ alkyl), NO$_2$, CO$_2$H, CO$_2$(C$_{1-4}$ alkyl), CONH$_2$, and CONH(C$_{1-4}$ alkyl);
R$^3$ is —(CH$_2$)$_Y$—CONH(C$_{3-6}$ carbocyclyl substituted with 0, 1, or 2 R$^7$), —(CH$_2$)$_Y$—CONH(4- to 6-membered heterocyclyl substituted with 0, 1, or 2 R$^7$), or —(CH$_2$)$_Y$—CONR$^e$R$^4$;
R$^e$ and R$^4$, taken together with the atoms to which they are attached, form a 5- or 6-membered azacyclyl comprising one or more carbon atoms and 1 to 4 heteroatoms selected from N, NR$^a$, O, and S(O)$_Z$, wherein the azacyclyl is substituted with 0, 1, or 2 R$^5$;
R$^6$ is, independently at each occurrence, selected from: OH, halogen, C$_{1-6}$ alkyl, C$_{1-4}$ alkoxy, C$_{1-4}$ haloalkyl, C$_{1-4}$ haloalkoxy, NH$_2$, NHR$^g$, OPh, OBn, Ph, —CONH$_2$; —CONHR$^i$; and —CONR$^h$R$^i$; or alternatively, two R$^6$, taken together with the atoms to which they are attached, form a 5- or 6-membered heterocyclyl; wherein the heterocyclyl comprises one or more carbon atoms and 1 to 4 heteroatoms selected from N, NR$^a$, O, and S(O)$_Z$, and is substituted with 0, 1, 2, or 3 R$^8$;
R$^7$, R$^8$, and R$^9$ are, independently at each occurrence, selected from: OH, halogen, C$_{1-6}$ alkyl, C$_{1-4}$ alkoxy, C$_{1-4}$ haloalkyl, C$_{1-4}$ haloalkoxy, NH$_2$, NH(C$_{1-4}$ alkyl), OPh, OBn, Ph, and a 5- or 6-membered heteroaryl comprising one or more carbon atoms and 1 to 4 heteroatoms selected from N, $NR^a$ and O;

$R^a$ is, independently at each occurrence, hydrogen, $C_{1-4}$ alkyl, or $C_{3-6}$ carbocyclyl;

$R^g$ is $C_{1-4}$ alkyl, $CO_2H$, $CO_2R^m$, $CONH_2$; $CONHR^p$;

$R^i$ is $C_{1-4}$ alkyl, $C_{1-4}$ alkoxy, $C_{1-4}$ haloalkyl, $C_{1-4}$ haloalkoxy; or alternatively, $R^h$ and $R^i$, taken together with the atoms to which they are attached, form a 5- or 6-membered azacyclyl comprising one or more carbon atoms and 1 to 4 heteroatoms selected from N, $NR^a$, O, and $S(O)_Z$), wherein the azacyclyl is substituted with 0, 1, or 2 $R^9$;

$R^m$ and $R^p$ are independently $C_{1-4}$ alkyl, $C_{3-6}$ carbocyclyl, $C_{1-4}$ alkoxy, $C_{1-4}$ haloalkyl, $C_1$-4 haloalkoxy, OPh, OBn, Ph, and a 5- or 6-membered heteroaryl comprising one or more carbon atoms and 1 to 4 heteroatoms selected from N, $NR^a$ and O;

X is 0, 1, or 2;

Y is 1 or 2;

Z is, independently at each occurrence, 0, 1, or 2; and

Q is, independently at each occurrence, 0 or 1.

10. The compound according to claim 9, wherein $R^3$ is —$(CH_2)$—$CONH(C_{3-6}$ cycloalkyl substituted with 0, 1, or 2 $R^7$), —$(CH_2)$—CONH(4- to 6-membered heterocycloalkyl substituted with 0, 1, or 2 $R^7$), or —$(CH_2)$—$CONR^eR^4$; and $R^e$ and $R^4$, taken together with the atoms to which they are attached, form a 5- or 6-membered azacyclyl comprising one or more carbon atoms and 1 to 4 heteroatoms selected from N, $NR^a$, O, and $S(O)_Z$, wherein the azacyclyl is substituted with 0, 1, or 2 $R^5$.

11. The compound according to claim 10, wherein $R^3$ is —$(CH_2)$—$CONHR^4$; and $R^4$ is cyclopropyl, cyclobutyl, cyclopentyl, oxetanyl, tetrahydrofuranyl, tetrahydropyranyl, azetidinyl, pyrrolidinyl, piperidinyl, morpholinyl, or piperazinyl, each of which is substituted with 0 or 1 $R^7$; or alternatively, $R^3$ is —$(CH_2)$—$CONR^eR^4$; and $R^e$ and $R^4$, taken together with the atoms to which they are attached, form azetidinyl, pyrrolidinyl, piperidinyl, morpholinyl, or piperazinyl, each of which is substituted with 0, 1, or 2 $R^5$.

12. The compound according to claim 9, wherein $R^h$ and R, taken together with the atoms to which they are attached, form azetidinyl, pyrrolidinyl, piperidinyl, morpholinyl, or piperazinyl, each of which is substituted with 0, 1, or 2 $R^9$.

13. The compound according to claim 9, wherein $R^6$ is, independently at each occurrence, selected from: OH, halogen, $C_{1-6}$ alkyl, $C_{1-4}$ alkoxy, $C_{1-4}$ haloalkyl, $C_{1-4}$ haloalkoxy, $NH_2$, $NHR^g$, OPh, OBn, Ph, —$CONH_2$, —$CONHR^i$; and —$CONR^hR^i$; or alternatively, two $R^6$, taken together with the atoms to which they are attached, form pyrrolidinonyl or pyridinonyl; each of which is substituted with 0, 1, or 2 $R^8$;

$R^g$ is $C_{1-4}$ alkyl, $CO_2R^m$, or $CONHR^p$;

$R^i$ is $C_{1-4}$ alkyl, $C_{1-4}$ alkoxy, $C_{1-4}$ haloalkyl, $C_{1-4}$ haloalkoxy; or alternatively, $R^h$ and $R^i$, taken together with the atoms to which they are attached, form azetidinyl, pyrrolidinyl, piperidinyl, morpholinyl, or piperazinyl, each of which is substituted with 0, 1, or 2 $R^9$;

$R^m$ and $R^p$ are independently $C_{1-4}$ alkyl, $C_{1-4}$ alkoxy, $C_{1-4}$ haloalkyl, or $C_{1-4}$ haloalkoxy; and Q is 0.

14. The compound according to claim 1, wherein $R^1$ is selected from the group consisting of

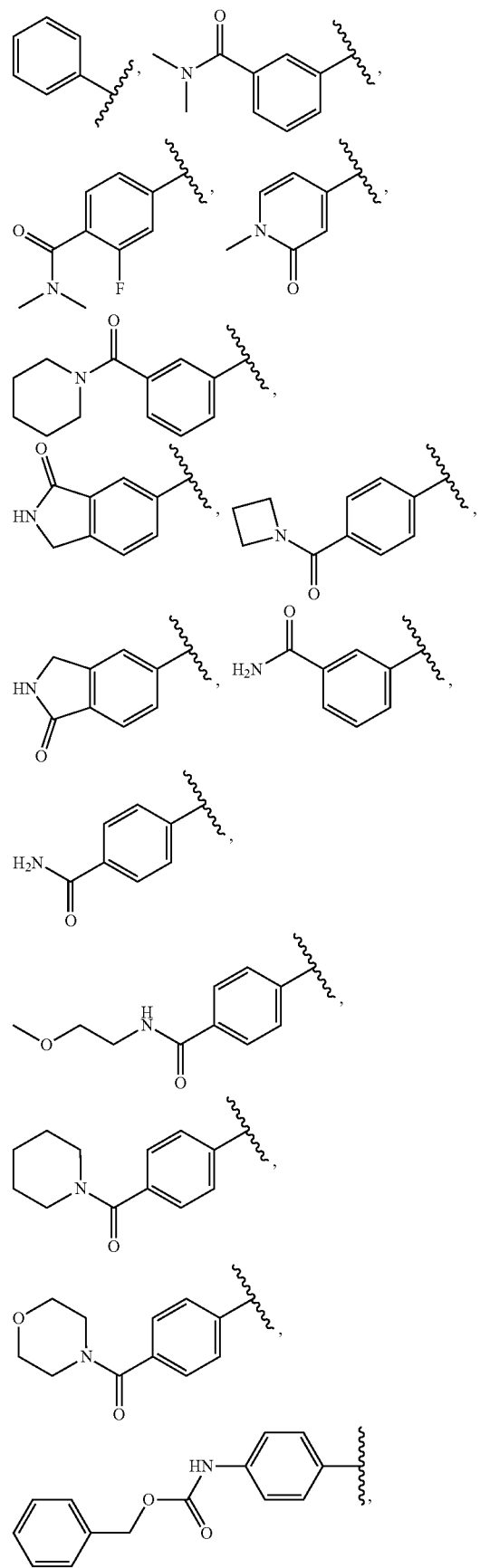

-continued

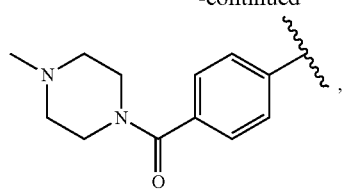,

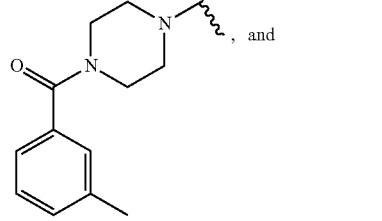,

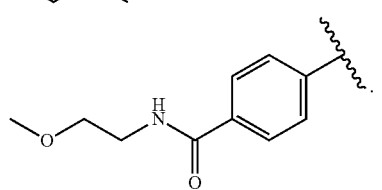, and

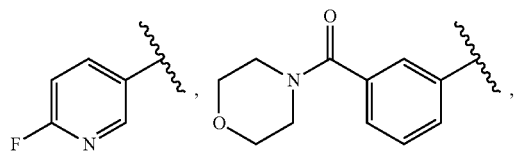.

15. The compound according to claim 1, wherein R³ is selected from the group consisting of

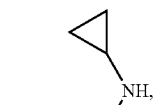
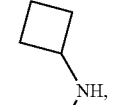
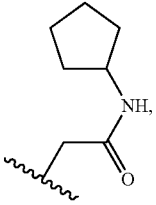

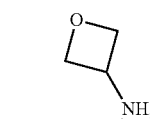
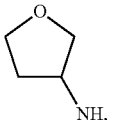
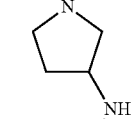

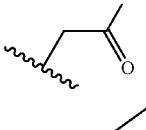, and 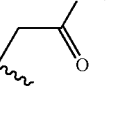

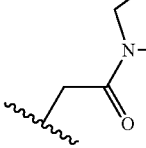, and 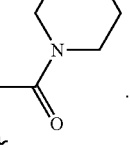.

16. The compound according to claim 1, which is selected from any one of Examples 1 to 29, or a stereoisomer, a tautomer, or a pharmaceutically acceptable salt or solvate thereof.

17. A pharmaceutical composition, comprising a pharmaceutically acceptable carrier and a compound according to claim 1, or a stereoisomer, a tautomer, or a pharmaceutically acceptable salt or solvate thereof.

* * * * *

UNITED STATES PATENT AND TRADEMARK OFFICE
CERTIFICATE OF CORRECTION

PATENT NO. : 10,597,370 B2  
APPLICATION NO. : 16/302158  
DATED : March 24, 2020  
INVENTOR(S) : Heather Finlay et al.

Page 1 of 1

It is certified that error appears in the above-identified patent and that said Letters Patent is hereby corrected as shown below:

In the Claims

Claim 12, Column 63, Line 45, delete "R," and insert -- $R^i$, --, therefor.

Signed and Sealed this  
Nineteenth Day of January, 2021

Andrei Iancu  
*Director of the United States Patent and Trademark Office*